(12) United States Patent
Yurek et al.

(10) Patent No.: US 7,988,735 B2
(45) Date of Patent: Aug. 2, 2011

(54) MECHANICAL APPARATUS AND METHOD FOR DELIVERING MATERIALS INTO THE INTER-VERTEBRAL BODY SPACE FOR NUCLEUS REPLACEMENT

(76) Inventors: Matthew Yurek, San Diego, CA (US);
Jerome Segal, Rockville, MD (US);
Kabir Gambhir, San Diego, CA (US);
Kurt Vedder, Danville, CA (US);
Robert Huffman, San Diego, CA (US)

( * ) Notice: Subject to any disclaimer, the term of this patent is extended or adjusted under 35 U.S.C. 154(b) by 437 days.

(21) Appl. No.: 12/316,789

(22) Filed: Dec. 16, 2008

(65) Prior Publication Data
US 2009/0105732 A1   Apr. 23, 2009

Related U.S. Application Data

(63) Continuation-in-part of application No. 11/700,509, filed on Jan. 31, 2007, and a continuation-in-part of application No. 11/153,776, filed on Jun. 15, 2005, and a continuation-in-part of application No. 11/272,299, filed on Nov. 10, 2005, and a continuation-in-part of application No. 11/359,335, filed on Feb. 22, 2006, now Pat. No. 7,547,319.

(51) Int. Cl.
*A61F 2/44* (2006.01)
(52) U.S. Cl. .................................................. 623/17.12
(58) Field of Classification Search .... 623/17.11–17.16, 623/16.11, 11.11; 606/41, 279, 92–94, 23.58, 606/246, 219, 220, 60, 277, 275, 63, 267, 606/266, 269, 278, 249, 250, 86 R; 604/528, 604/95.02–95.04
See application file for complete search history.

(56) References Cited

U.S. PATENT DOCUMENTS

| | | | | |
|---|---|---|---|---|
| 3,875,595 A * | 4/1975 | Froning | ..................... | 623/17.12 |
| 4,772,287 A * | 9/1988 | Ray et al. | ................... | 623/17.12 |
| 5,108,404 A * | 4/1992 | Scholten et al. | ................ | 606/94 |
| 5,171,280 A * | 12/1992 | Baumgartner | ............. | 623/17.12 |
| 5,549,679 A * | 8/1996 | Kuslich | ........................ | 623/17.12 |
| 5,571,189 A * | 11/1996 | Kuslich | ........................ | 623/17.12 |
| 5,718,702 A * | 2/1998 | Edwards | ......................... | 606/41 |
| 5,730,127 A * | 3/1998 | Avitall | .......................... | 600/374 |
| 5,785,705 A * | 7/1998 | Baker | ............................. | 606/32 |
| 5,836,947 A * | 11/1998 | Fleischman et al. | ............ | 606/47 |
| 5,863,291 A * | 1/1999 | Schaer | ........................... | 606/41 |
| 5,879,295 A * | 3/1999 | Li et al. | .......................... | 600/373 |
| 6,071,274 A * | 6/2000 | Thompson et al. | ........... | 604/528 |
| 6,183,518 B1 * | 2/2001 | Ross et al. | .................. | 623/17.16 |
| 6,235,043 B1 * | 5/2001 | Reiley et al. | .................. | 606/192 |
| 6,248,131 B1 * | 6/2001 | Felt et al. | .................... | 623/17.12 |
| 6,264,659 B1 * | 7/2001 | Ross et al. | ...................... | 606/93 |
| 6,332,880 B1 * | 12/2001 | Yang et al. | .................... | 604/528 |
| 6,375,659 B1 * | 4/2002 | Erbe et al. | ....................... | 606/94 |
| 6,395,034 B1 * | 5/2002 | Suddaby | ................... | 623/17.15 |
| 6,428,576 B1 * | 8/2002 | Haldimann | ................ | 623/17.16 |

(Continued)

*Primary Examiner* — Alvin J. Stewart
(74) *Attorney, Agent, or Firm* — Michael Klicpera

(57) ABSTRACT

The present invention relates to a device and method to perform 1) disk fusing, 2) an artificial replacement of the nucleus, 3) artificial replacement of the annulus, or 4), an artificial replacement of both the nucleus and annulus. The device is designed to be placed into the inter-vertebral space following discectomy. The invention includes a delivery catheter and an expandable continuous mesh that has a torus configuration with a lumen within the mesh and a center hole. The mesh can be diametrically expanded in diameter into the disc space whereby various materials can be injected into the lumen and/or the center hole.

35 Claims, 14 Drawing Sheets

U.S. PATENT DOCUMENTS

| | | | |
|---|---|---|---|
| 6,436,143 B1* | 8/2002 | Ross et al. | 623/17.16 |
| 6,464,700 B1* | 10/2002 | Koblish et al. | 606/41 |
| 6,508,839 B1* | 1/2003 | Lambrecht et al. | 623/17.16 |
| 6,533,817 B1* | 3/2003 | Norton et al. | 623/17.16 |
| 6,582,467 B1* | 6/2003 | Teitelbaum et al. | 623/17.11 |
| 6,607,505 B1* | 8/2003 | Thompson et al. | 604/95.04 |
| 6,613,046 B1* | 9/2003 | Jenkins et al. | 606/41 |
| 6,620,196 B1* | 9/2003 | Trieu | 623/17.16 |
| 6,733,496 B2* | 5/2004 | Sharkey et al. | 606/41 |
| 6,733,531 B1* | 5/2004 | Trieu | 623/17.11 |
| 6,733,533 B1* | 5/2004 | Lozier | 623/17.12 |
| 6,764,514 B1* | 7/2004 | Li et al. | 623/17.12 |
| 6,783,546 B2* | 8/2004 | Zucherman et al. | 623/17.16 |
| 6,878,155 B2* | 4/2005 | Sharkey et al. | 607/96 |
| 6,893,466 B2* | 5/2005 | Trieu | 623/17.16 |
| 6,899,719 B2* | 5/2005 | Reiley et al. | 606/192 |
| 6,916,306 B1* | 7/2005 | Jenkins et al. | 604/95.04 |
| 6,932,843 B2* | 8/2005 | Smith et al. | 623/17.11 |
| 6,969,404 B2* | 11/2005 | Ferree | 623/17.11 |
| 6,976,979 B2* | 12/2005 | Lawrence et al. | 604/524 |
| 6,979,341 B2* | 12/2005 | Scribner et al. | 606/192 |
| 7,001,431 B2* | 2/2006 | Bao et al. | 623/17.12 |
| 7,004,970 B2* | 2/2006 | Cauthen, III et al. | 623/17.16 |
| 7,008,401 B2* | 3/2006 | Thompson et al. | 604/95.04 |
| 7,029,471 B2* | 4/2006 | Thompson et al. | 606/41 |
| 7,044,954 B2* | 5/2006 | Reiley et al. | 606/93 |
| 7,066,960 B1* | 6/2006 | Dickman | 623/17.16 |
| 7,077,865 B2* | 7/2006 | Bao et al. | 623/17.12 |
| 7,175,619 B2* | 2/2007 | Koblish et al. | 606/41 |
| 7,267,692 B2* | 9/2007 | Fortin et al. | 623/17.16 |
| 7,306,610 B2* | 12/2007 | Chern Lin et al. | 606/92 |
| 7,318,840 B2* | 1/2008 | McKay | 623/17.11 |
| 7,322,962 B2* | 1/2008 | Forrest | 604/164.01 |
| 7,427,295 B2* | 9/2008 | Ellman et al. | 623/17.16 |
| 7,442,210 B2* | 10/2008 | Segal et al. | 623/17.12 |
| 7,465,318 B2* | 12/2008 | Sennett et al. | 623/17.12 |
| 7,507,243 B2* | 3/2009 | Lambrecht et al. | 606/99 |
| 7,520,888 B2* | 4/2009 | Trieu | 606/279 |
| 7,534,268 B2* | 5/2009 | Hudgins et al. | 623/17.12 |
| 7,544,196 B2* | 6/2009 | Bagga et al. | 606/93 |
| 7,547,319 B2* | 6/2009 | Segal et al. | 606/279 |
| 7,547,326 B2* | 6/2009 | Bhatnagar et al. | 623/17.16 |
| 7,553,307 B2* | 6/2009 | Bleich et al. | 606/1 |
| 7,575,577 B2* | 8/2009 | Boyd et al. | 606/92 |
| 7,597,714 B2* | 10/2009 | Suddaby | 623/17.16 |
| 7,601,157 B2* | 10/2009 | Boyd et al. | 606/92 |
| 7,601,172 B2* | 10/2009 | Segal et al. | 623/17.11 |
| 7,618,457 B2* | 11/2009 | Hudgins | 623/17.12 |
| 7,618,461 B2* | 11/2009 | Trieu | 623/17.16 |
| 7,632,294 B2* | 12/2009 | Milbodker et al. | 606/279 |
| 7,645,301 B2* | 1/2010 | Hudgins et al. | 623/17.12 |
| 7,699,894 B2* | 4/2010 | O'Neil et al. | 623/17.12 |
| 7,713,301 B2* | 5/2010 | Bao et al. | 623/17.12 |
| 7,717,918 B2* | 5/2010 | Truckai et al. | 606/94 |
| 7,717,956 B2* | 5/2010 | Lang | 623/14.12 |
| 7,717,958 B2* | 5/2010 | Cragg et al. | 623/17.12 |
| 7,731,681 B2* | 6/2010 | Schaer et al. | 604/95.04 |
| 7,758,647 B2* | 7/2010 | Arnin et al. | 623/17.16 |
| 7,780,734 B2* | 8/2010 | Johnson et al. | 623/17.16 |
| 7,785,368 B2* | 8/2010 | Schaller | 623/17.11 |
| 7,789,912 B2* | 9/2010 | Manzi et al. | 623/17.11 |
| 7,799,056 B2* | 9/2010 | Sankaran | 606/246 |
| 7,799,078 B2* | 9/2010 | Embry et al. | 623/17.11 |
| 7,799,833 B2* | 9/2010 | Boyd | 514/564 |
| 7,824,444 B2* | 11/2010 | Biscup et al. | 623/17.12 |
| 7,837,733 B2* | 11/2010 | Collins et al. | 623/17.12 |
| 7,842,040 B2* | 11/2010 | Rabiner et al. | 606/92 |
| 7,842,095 B2* | 11/2010 | Klein | 623/23.19 |
| 7,857,808 B2* | 12/2010 | Oral et al. | 606/41 |
| 7,867,278 B2* | 1/2011 | Lambrecht et al. | 623/17.11 |
| 7,883,511 B2* | 2/2011 | Fernyhough | 606/92 |
| 7,887,593 B2* | 2/2011 | McKay et al. | 623/17.16 |
| 7,901,460 B2* | 3/2011 | Sherman | 623/17.16 |
| 7,905,863 B1* | 3/2011 | Forrest | 604/164.01 |
| 7,914,537 B2* | 3/2011 | Boyd et al. | 606/92 |
| 7,914,538 B2* | 3/2011 | Howe | 606/104 |
| 2002/0026195 A1* | 2/2002 | Layne et al. | 606/72 |
| 2002/0049449 A1* | 4/2002 | Bhatnagar et al. | 606/94 |
| 2002/0077701 A1* | 6/2002 | Kuslich | 623/17.12 |
| 2002/0147496 A1* | 10/2002 | Belef et al. | 623/17.12 |
| 2002/0147497 A1* | 10/2002 | Belef et al. | 623/17.12 |
| 2002/0173851 A1* | 11/2002 | McKay | 623/17.11 |
| 2003/0088249 A1* | 5/2003 | Furderer | 606/61 |
| 2003/0195628 A1* | 10/2003 | Bao et al. | 623/17.12 |
| 2004/0054413 A1* | 3/2004 | Higham et al. | 623/17.16 |
| 2004/0059417 A1* | 3/2004 | Smith et al. | 623/17.11 |
| 2004/0068268 A1* | 4/2004 | Boyd et al. | 606/92 |
| 2004/0106999 A1* | 6/2004 | Mathews | 623/17.16 |
| 2004/0127992 A1* | 7/2004 | Serhan et al. | 623/17.16 |
| 2004/0143333 A1* | 7/2004 | Bain et al. | 623/17.16 |
| 2004/0167625 A1* | 8/2004 | Beyar et al. | 623/11.11 |
| 2004/0186471 A1* | 9/2004 | Trieu | 606/61 |
| 2004/0215344 A1* | 10/2004 | Hochschuler et al. | 623/17.12 |
| 2004/0230309 A1* | 11/2004 | DiMauro et al. | 623/17.12 |
| 2004/0260397 A1* | 12/2004 | Lambrecht et al. | 623/17.16 |
| 2004/0267368 A1* | 12/2004 | Kuslich | 623/17.16 |
| 2005/0004515 A1* | 1/2005 | Hart et al. | 604/95.04 |
| 2005/0010297 A1* | 1/2005 | Watson et al. | 623/17.12 |
| 2005/0015150 A1* | 1/2005 | Lee | 623/17.12 |
| 2005/0038514 A1* | 2/2005 | Helm et al. | 623/17.12 |
| 2005/0049592 A1* | 3/2005 | Keith et al. | 606/61 |
| 2005/0049604 A1* | 3/2005 | Singer et al. | 606/90 |
| 2005/0065609 A1* | 3/2005 | Wardlaw | 623/17.12 |
| 2005/0090901 A1* | 4/2005 | Studer | 623/17.12 |
| 2005/0113923 A1* | 5/2005 | Acker et al. | 623/17.12 |
| 2005/0154463 A1* | 7/2005 | Trieu | 623/17.16 |
| 2005/0182418 A1* | 8/2005 | Boyd et al. | 606/92 |
| 2005/0209557 A1* | 9/2005 | Carroll et al. | 604/95.04 |
| 2005/0209595 A1* | 9/2005 | Karmon | 606/76 |
| 2005/0234498 A1* | 10/2005 | Gronemeyer et al. | 606/192 |
| 2005/0245938 A1* | 11/2005 | Kochan | 606/92 |
| 2005/0251259 A1* | 11/2005 | Suddaby | 623/17.12 |
| 2005/0278027 A1* | 12/2005 | Hyde, Jr. | 623/17.12 |
| 2005/0283246 A1* | 12/2005 | Cauthen et al. | 623/17.16 |
| 2006/0052874 A1* | 3/2006 | Johnson et al. | 623/17.16 |
| 2006/0084983 A1* | 4/2006 | Kim | 606/61 |
| 2006/0084988 A1* | 4/2006 | Kim | 606/61 |
| 2006/0085069 A1* | 4/2006 | Kim | 623/17.11 |
| 2006/0106461 A1* | 5/2006 | Embry et al. | 623/17.12 |
| 2006/0116767 A1* | 6/2006 | Magerl et al. | 623/17.12 |
| 2006/0122704 A1* | 6/2006 | Vresilovic et al. | 623/17.16 |
| 2006/0149279 A1* | 7/2006 | Mathews | 606/90 |
| 2006/0149379 A1* | 7/2006 | Kuslich et al. | 623/17.12 |
| 2006/0149380 A1* | 7/2006 | Lotz et al. | 623/17.12 |
| 2006/0173545 A1* | 8/2006 | Cauthen et al. | 623/17.16 |
| 2006/0195115 A1* | 8/2006 | Ferree | 606/92 |
| 2006/0235523 A1* | 10/2006 | Gil | 623/17.12 |
| 2006/0247780 A1* | 11/2006 | Bert | 623/17.16 |
| 2006/0253198 A1* | 11/2006 | Myint et al. | 623/17.12 |
| 2006/0255503 A1* | 11/2006 | Higham et al. | 264/255 |
| 2006/0287726 A1* | 12/2006 | Segal et al. | 623/17.12 |
| 2007/0055265 A1* | 3/2007 | Schaller | 606/86 |
| 2007/0055272 A1* | 3/2007 | Schaller | 606/90 |
| 2007/0093899 A1* | 4/2007 | Dutoit et al. | 623/17.11 |
| 2007/0173943 A1* | 7/2007 | Dulak et al. | 623/17.16 |
| 2007/0233222 A1* | 10/2007 | Roeder et al. | 623/1.11 |
| 2008/0051800 A1* | 2/2008 | Diaz et al. | 606/92 |
| 2008/0091199 A1* | 4/2008 | Cragg | 606/60 |
| 2008/0103505 A1* | 5/2008 | Fransen | 606/92 |
| 2008/0132899 A1* | 6/2008 | Shadduck et al. | 606/94 |
| 2008/0132934 A1* | 6/2008 | Reiley et al. | 606/192 |
| 2008/0133012 A1* | 6/2008 | McGuckin | 623/17.12 |
| 2008/0140084 A1* | 6/2008 | Osorio et al. | 606/94 |
| 2008/0195207 A1* | 8/2008 | Lin et al. | 623/17.12 |
| 2008/0208341 A1* | 8/2008 | McCormack et al. | 623/17.12 |
| 2008/0215151 A1* | 9/2008 | Kohm et al. | 623/17.11 |
| 2008/0228135 A1* | 9/2008 | Snoderly | 604/95.04 |
| 2008/0243249 A1* | 10/2008 | Kohm et al. | 623/17.12 |
| 2008/0249604 A1* | 10/2008 | Donovan et al. | 623/1.15 |
| 2008/0269761 A1* | 10/2008 | Truckai et al. | 606/94 |
| 2008/0269795 A1* | 10/2008 | Reiley et al. | 606/192 |
| 2008/0269796 A1* | 10/2008 | Reiley et al. | 606/192 |
| 2008/0300687 A1* | 12/2008 | Lin et al. | 623/17.12 |
| 2009/0030399 A1* | 1/2009 | Raiszadeh | 604/506 |
| 2009/0054990 A1* | 2/2009 | Myint et al. | 623/17.16 |
| 2009/0069899 A1* | 3/2009 | Klein | 623/22.4 |
| 2009/0076518 A1* | 3/2009 | Bowman et al. | 606/93 |

| | | | | | | |
|---|---|---|---|---|---|---|
| 2009/0076610 A1* | 3/2009 | Afzal ............... 623/17.16 | 2010/0145454 A1* | 6/2010 | Hoffman ............... 623/17.12 |
| 2009/0112221 A1* | 4/2009 | Burke et al. ............... 606/102 | 2010/0168858 A1* | 7/2010 | Hardenbrook et al. .... 623/17.12 |
| 2009/0112323 A1* | 4/2009 | Hestad et al. ............... 623/17.12 | 2010/0168859 A1* | 7/2010 | Wardlaw ............... 623/17.12 |
| 2009/0125031 A1* | 5/2009 | Melsheimer et al. ........... 606/94 | 2010/0174375 A1* | 7/2010 | Schaller ............... 623/17.16 |
| 2009/0156995 A1* | 6/2009 | Martin et al. ............... 604/95.04 | 2010/0185286 A1* | 7/2010 | Allard et al. ............... 623/17.11 |
| 2009/0182268 A1* | 7/2009 | Thielen et al. ............... 604/95.04 | 2010/0204794 A1* | 8/2010 | Jarzem et al. ............... 623/17.12 |
| 2009/0182386 A1* | 7/2009 | Schaller ............... 606/86 R | 2010/0222824 A1* | 9/2010 | Simonson ............... 606/279 |
| 2009/0187249 A1* | 7/2009 | Osman ............... 623/17.16 | 2010/0228239 A1* | 9/2010 | Freed ............... 606/27 |
| 2009/0204216 A1* | 8/2009 | Biedermann et al. ...... 623/17.12 | 2010/0256646 A1* | 10/2010 | Pinal et al. ............... 606/92 |
| 2009/0222093 A1* | 9/2009 | Liu et al. ............... 623/17.12 | 2010/0256647 A1* | 10/2010 | Trieu ............... 606/92 |
| 2009/0222097 A1* | 9/2009 | Liu et al. ............... 623/17.16 | 2010/0262242 A1* | 10/2010 | Chavatte et al. ............ 623/17.12 |
| 2009/0234457 A1* | 9/2009 | Lotz et al. ............... 623/17.16 | 2010/0305703 A1* | 12/2010 | Lin ............... 623/17.12 |
| 2009/0299476 A1* | 12/2009 | Diwan et al. ............... 623/17.12 | 2010/0318189 A1* | 12/2010 | Edie et al. ............... 623/17.12 |
| 2009/0312697 A1* | 12/2009 | Zemlock ............... 604/95.04 | 2011/0004308 A1* | 1/2011 | Marino et al. ............... 623/17.12 |
| 2010/0069734 A1* | 3/2010 | Worley et al. ............... 600/374 | 2011/0009971 A1* | 1/2011 | Johnson et al. ............ 623/17.16 |
| 2010/0106155 A1* | 4/2010 | Anderson et al. ............... 606/41 | 2011/0066105 A1* | 3/2011 | Hart et al. ............... 604/95.04 |
| 2010/0137990 A1* | 6/2010 | Apatsidis et al. ........... 623/17.16 | * cited by examiner | | |

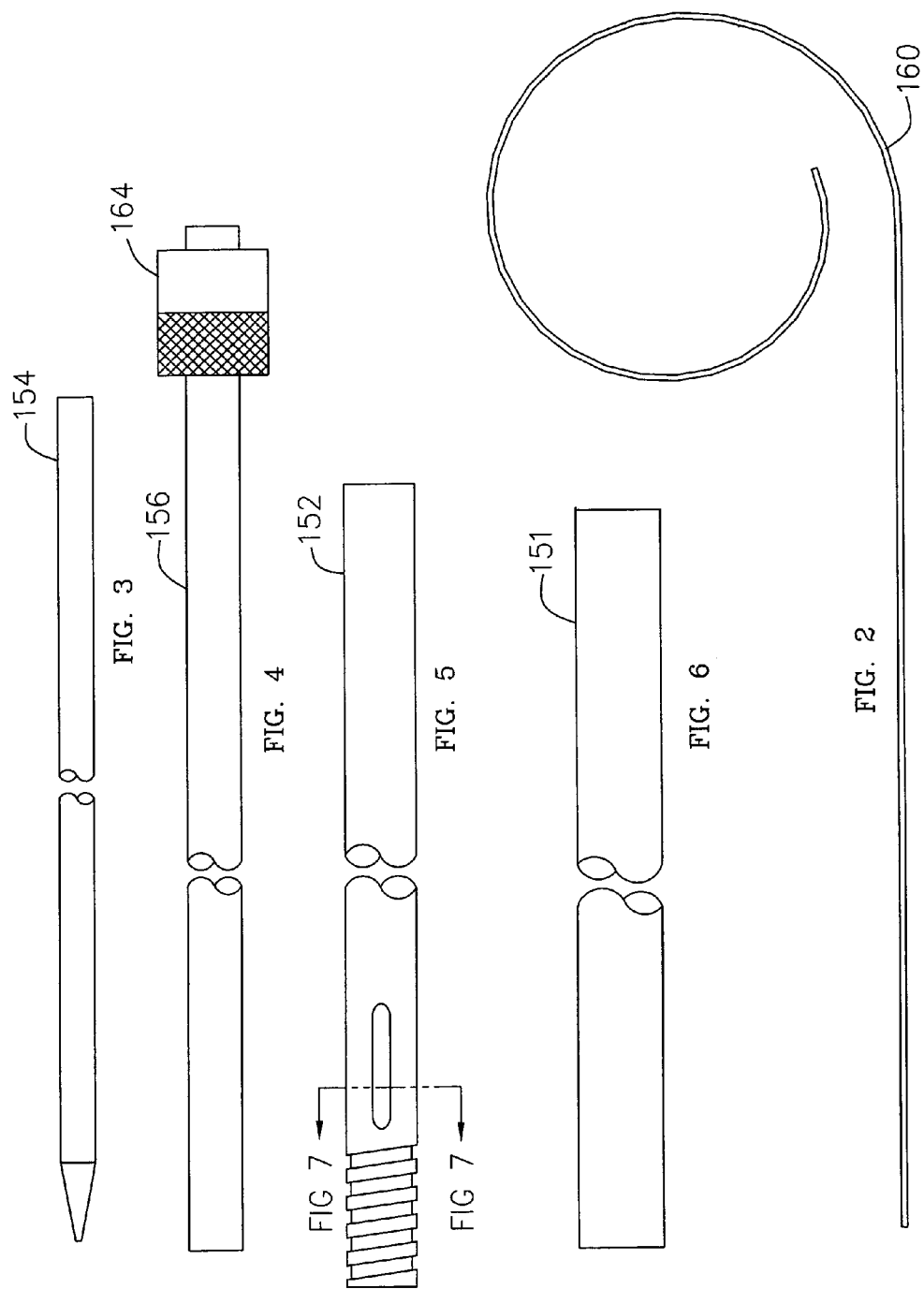

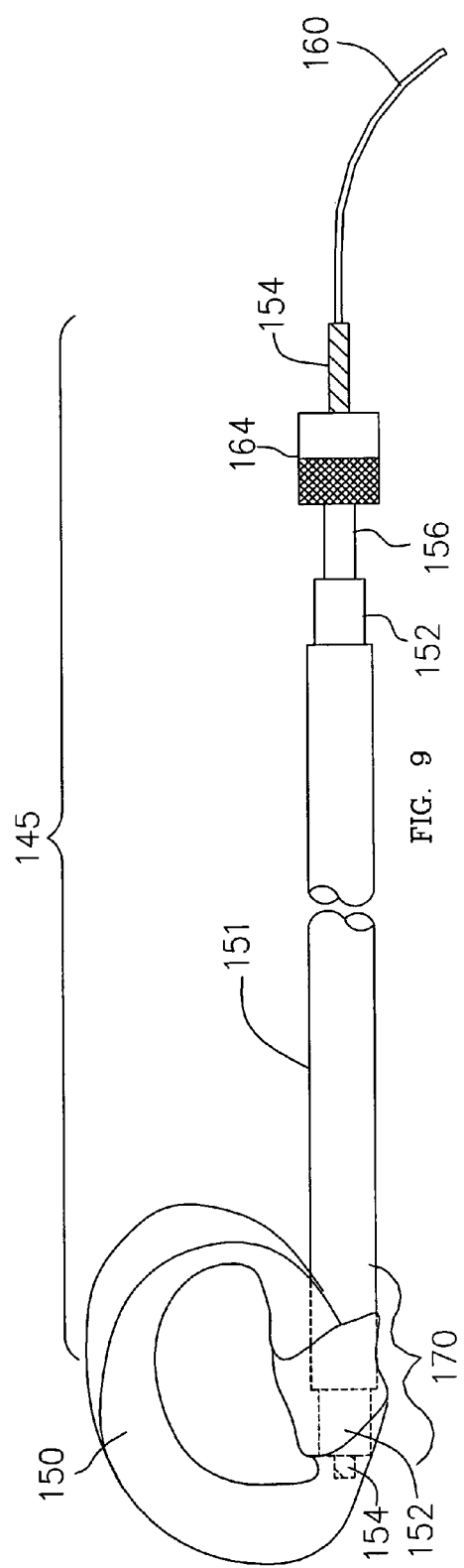
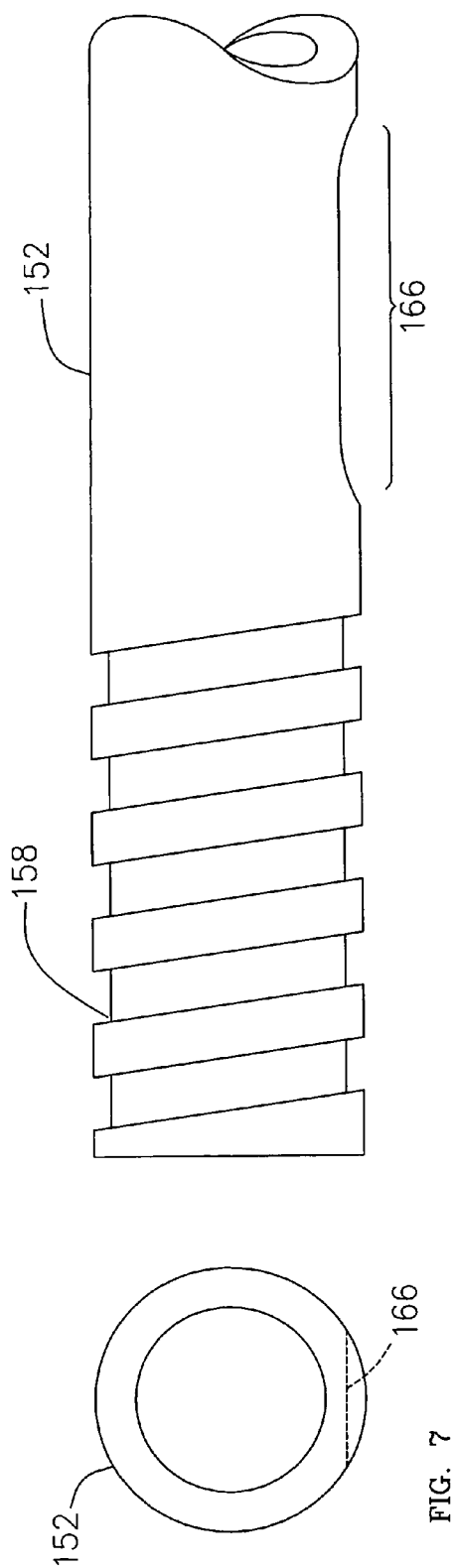
FIG. 7
FIG. 8
FIG. 9

MECHANICAL APPARATUS AND METHOD
FOR DELIVERING MATERIALS INTO THE
INTER-VERTEBRAL BODY SPACE FOR
NUCLEUS REPLACEMENT

CROSS-REFERENCES

The present application is a continuation-in-part of patent application Ser. No. 11/153,776 filed on Jun. 15, 2005, Ser. No. 11/272,299 filed on Nov. 10, 2005, Ser. No. 11/359,335 filed on Feb. 22, 2006 now U.S. Pat. No. 7,547,319 and Ser. No. 11/700,509 filed on Jan. 31, 2007. These applications are incorporated herein by this reference.

FIELD OF THE INVENTION

The present invention generally relates to devices and methods for the repair of inter-vertebral discs. More, specifically, the present invention relates to devices and methods for the treatment of spinal disorders associated with the nucleus, annulus and inter-vertebral disc.

BACKGROUND OF THE INVENTION

Inter-vertebral disc disease is a major worldwide health problem. In the United States alone almost 700,000 spine procedures are performed each year and the total cost of treatment of back pain exceeds $30 billion. Age related changes in the disc include diminished water content in the nucleus and increased collagen content by the $4^{th}$ decade of life. Loss of water binding by the nucleus results in more compressive loading of the annulus. This renders the annulus more susceptible to delamination and damage. Damage to the annulus, in turn, accelerates disc degeneration and degeneration of surrounding tissues such as the facet joints.

The two most common spinal surgical procedures performed are discectomy and spinal fusion. These procedures only address the symptom of lower back pain. Both procedures actually worsen the overall condition of the affected disc and the adjacent discs. A better solution would be implantation of an artificial disc for treatment of the lower back pain and to restore the normal anatomy and function of the diseased disc.

The concept of a disc prosthesis dates back to a French patent by van Steenbrugghe in 1956. 17 years later, Urbaniak reported the first disc prosthesis implanted in animals. Since this time, numerous prior art devices for disc replacement have been proposed and tested. These are generally divided into devices for artificial total disc replacement or artificial nucleus replacement. The devices proposed for artificial total disc replacement, such as those developed by Kostuik, that generally involve some flexible central component attached to metallic endplates which may be affixed to the adjacent vertebrae. The flexible component may be in the form of a spring or alternatively a polyethylene core (Marnay). The most widely implanted total artificial disc to date is the Link SB Charite disc which is composed of a biconvex ultra high molecular weight polyethylene spacer interfaced with two endplates made of cobalt-chromium-molybdenum alloy. Over 2000 of these have been implanted with good results. However device failure has been reported along with dislocation and migration. The Charite disc also requires an extensive surgical dissection via an anterior approach.

The approach of artificial nucleus replacement has several obvious advantages over artificial total disc replacement. By replacing only the nucleus, it preserves the remaining disc structures such as the annulus and endplates and preserves their function. Because the annulus and endplates are left intact, the surgical procedure is much simpler and operative time is less. Several nuclear prostheses can be placed via a minimally invasive endoscopic approach. The nucleus implant in widest use today is the one developed by Raymedica (Bloomington, Minn.) which consists of a hydrogel core constrained in a woven polyethylene jacket. The pellet shaped hydrogel core is compressed and dehydrated to minimize size prior to placement. Upon implantation the hydrogel begins to absorb fluid and expand. The flexible but inelastic jacket permits the hydrogel to deform and reform in response to compressive forces yet constrain the horizontal and vertical expansion (see U.S. Pat. Nos. 4,904,260 and 4,772,287 to Ray). Other types of nuclear replacement have been described which include either an expansive hydrogel or polymer to provide for disc separation and relieve compressive load on the other disc components (see U.S. Pat. No. 5,192,326 to Boa). Major limitations of nuclear prostheses are that they can only be used in patients in whom disc degeneration is at an early stage because they require the presence of a competent natural annulus. In discs at later stages of degeneration the annulus is often torn, flattened and/or delaminated and may not be strong enough to provide the needed constraint. Additionally, placement of the artificial nucleus often requires access through the annulus. This leaves behind a defect in the annulus through which the artificial nucleus may eventually extrude compressing adjacent structures. What is clearly needed is a replacement or reinforcement for the natural annulus which may be used in conjunction with these various nuclear replacement devices.

Several annular repair or reinforcement devices have been previously described. These include the annulus reinforcing band described by U.S. Pat. No. 6,712,853 to Kuslich, which describes an expansile band pressurized with bone graft material or like, expanding the band. U.S. Pat. No. 6,883,520B2 to Lambrecht et al, describes a device and method for constraining a disc herniation utilizing an anchor and membrane to close the annular defect. U.S. patent application Ser. No. 10/676,868 to Slivka et al. describes a spinal disc defect repair method. U.S. Pat. No. 6,806,595 B2 to Keith et al. describes disc reinforcement by implantation of reinforcement members around the annulus of the disc. U.S. Pat. No. 6,592,625 B2 to Cauthen describes a collapsible patch put through an aperture in the subannular space. U.S. patent application Ser. No. 10/873,899 to Milbocker et al. describes injection of in situ polymerizing fluid for repair of a weakened annulus fibrosis or replacement or augmentation of the disc nucleus.

Each of these prior art references describes devices or methods utilized for repair of at least a portion of the diseased annulus. What is clearly needed is an improved spinal disc device and method capable of reinforcing the entire annulus circumferentially. In addition what is clearly needed is a spinal disc device and method which may be easily placed into the inter-vertebral space and made to conform to this space. The need for an improved spinal disc device and method capable of reinforcing the entire annulus that may be utilized either in conjunction with an artificial nucleus pulposis or may be used as a reinforcement for the annulus fibrosis and as an artificial nucleus pulposis is evident.

SUMMARY OF THE INVENTION

The present invention addresses these needs by providing improved spinal disc device and methods for the treatment of inter-vertebral disc disease. The improved device and methods of the present invention specifically address disc related pain but may have other significant applications not specifically mentioned herein. For purposes of illustration only, and without limitation, the present invention is discussed in detail with reference to the treatment of damaged discs of the adult human spinal column.

As will become apparent from the following detailed description, the improved spinal disc device and methods of the present invention may reduce if not eliminate back pain while maintaining near normal anatomical motion. The present invention relates to devices and methods which may be used to reinforce or replace the native annulus, replace the native nucleus, replace both the annulus and nucleus or facilitate fusion of adjacent vertebrae. The devices of the present invention are particularly well suited for minimally invasive methods of implantation.

The spinal disc device is a catheter based device with a unique delivery system which is placed into the intervertebral space following discectomy performed by either traditional surgical or endoscopic approaches. The distal end of the catheter is comprised of an expandable loop or mesh that is removably attached to a delivery tubular member using a screw threaded section. Coaxially within the delivery tubular member is an injection tubular member, an introducer tubular member and a guiding member. The expandable loop or mesh may be increased in diameter by advancement of the introducer tubular member and/or the injection tubular member. The expandable loop or mesh may be formed of a woven, knitted, embroidered or braided material and may be made of PEEK (polyetheretherketone), Nylon, Dacron, synthetic polyamide, polypropylene, polyolefin (e.g. heat shrink tubing), Teflon (PTFE), polyurethane, Pebax, Hytrel, expanded polytetrafluroethylene (e-PTFE), polyethylene and ultra-high molecular weight fibers of polyethylene (UHMWPE) commercially available as Spectra™ or Dyneema™, as well as other high tensile strength materials such as Vectran™, Kevlar™, natural or artificially produced silk and commercially available suture materials used in a variety of surgical procedures. Alternatively the expansile loop or mesh portion of the catheter may be made of a biodegradable or bioabsorbable material such as resorbable collagen, LPLA (poly(l-lactide)), DLPLA (poly(dl-lactide)), LPLA-DLPLA, PGA (polyglycolide), PGA-LPIA or PGA-DLPLA, polylactic acid and polyglycolic acid which is broken down and bioabsorbed by the patient over a period of time. Alternatively the expansile portion of the catheter may be formed from metallic materials, for example, stainless steel, Elgiloy™, Nitinol, or other biocompatible metals. Further, it is anticipated that the expansile loop portion of the device could be made from a flattened tubular knit, weave, mesh or foam structure.

The expandable loop or mesh is formed such that one end of the loop feeds into its other end (overlapping), similar to a snake eating its own tail forming the shape of a toroid with an inner chamber and a central open area. The overlapping section of the expandable mesh has a threaded nut section which engages the screw threads of the delivery tubular member and provides for the introducer tubular member, the injection tubular member, and the guiding member to have access to the inner chamber of the expandable mesh.

Once one or more materials are delivered or injected into the inner chamber, the expandable loop or mesh can be detached from the deliver components (delivery tubular member, introducer deliver member, injection tubular member, and guiding member) by unscrewing the delivery tubular member from the threaded nut section of the expandable loop or mesh. Due to the design that one end of the loop feeds into its other end (overlapping), once the delivery tubular member is detached, the thread net section with access to the inner chamber will become self-closes.

The present invention consists of a device and method, whereby the present invention is first delivered and expanded within the inter-vertebral space to the limits of the inner portion of the native annulus to artificially replace all or a portion of a damaged nucleus.

The present invention consists of a device and method, whereby the invention is first delivered and expanded within the inter-vertebral space to the limits of the inner portion of the native annulus and then an injection of polymeric or hydrogel or like material is conducted to reinforce or artificially replace the native annulus.

The present invention also consists of a device and method, whereby the invention is first delivered within the inter-vertebral space and into the area of the nucleus, which may have been previously removed, and expanded to the limits of the outer portion of the area of the native nucleus and then injected with a polymer or hydrogel or like material conducted to reinforce or artificially replace the native nucleus.

The present invention also consists of a device and method, whereby the invention is first delivered within the inter-vertebral space and expanded within the inter-vertebral space to the limits of the outer portion of the native annulus and then an injection of polymeric or hydrogel material is conducted to reinforce or artificially replace the native annulus. Then the present invention is delivered into the nucleus area and expanded to the limits of the outer portion of the native nucleus or an artificial nucleus concurrently placed and then an injection of polymeric or hydrogel material is conducted to reinforce or artificially replace or reinforce the nucleus.

The present invention and variations of its embodiments is summarized herein. Additional details of the present invention and embodiments of the present invention may be found in the Detailed Description of the Preferred Embodiments and Claims below. These and other features, aspects and advantages of the present invention will become better understood with reference to the following descriptions and claims.

BRIEF DESCRIPTION OF THE DRAWINGS

FIG. 2 is a side view of the guiding member.

FIG. 3 is a side view of the introducer tubular member.

FIG. 4 is a side view of the injection tubular member proximately fitted with a luer connector.

FIG. 5 is a side view of the delivery tubular member distally fitted with a first and second engagement means.

FIG. 6 is a side view of the collet tubular member.

FIG. 7 is a cross-sectional view of FIG. 5 showing a flattened section of the delivery tubular member whereby the guiding member is physically engaged by the collet tubular member.

FIG. 8 is an exploded view of distal end of FIG. 5 further showing the screw thread first engagement means and a second flattened section engagement means on the delivery tubular member.

FIG. 9 is a side view of the present invention showing, in general the present invention with an expandable mesh, the collet tubular member, the delivery tubular member, the introducer tubular member, the injection tubular member and the guiding member.

DESCRIPTION OF THE PREFERRED EMBODIMENTS

Figure 1:
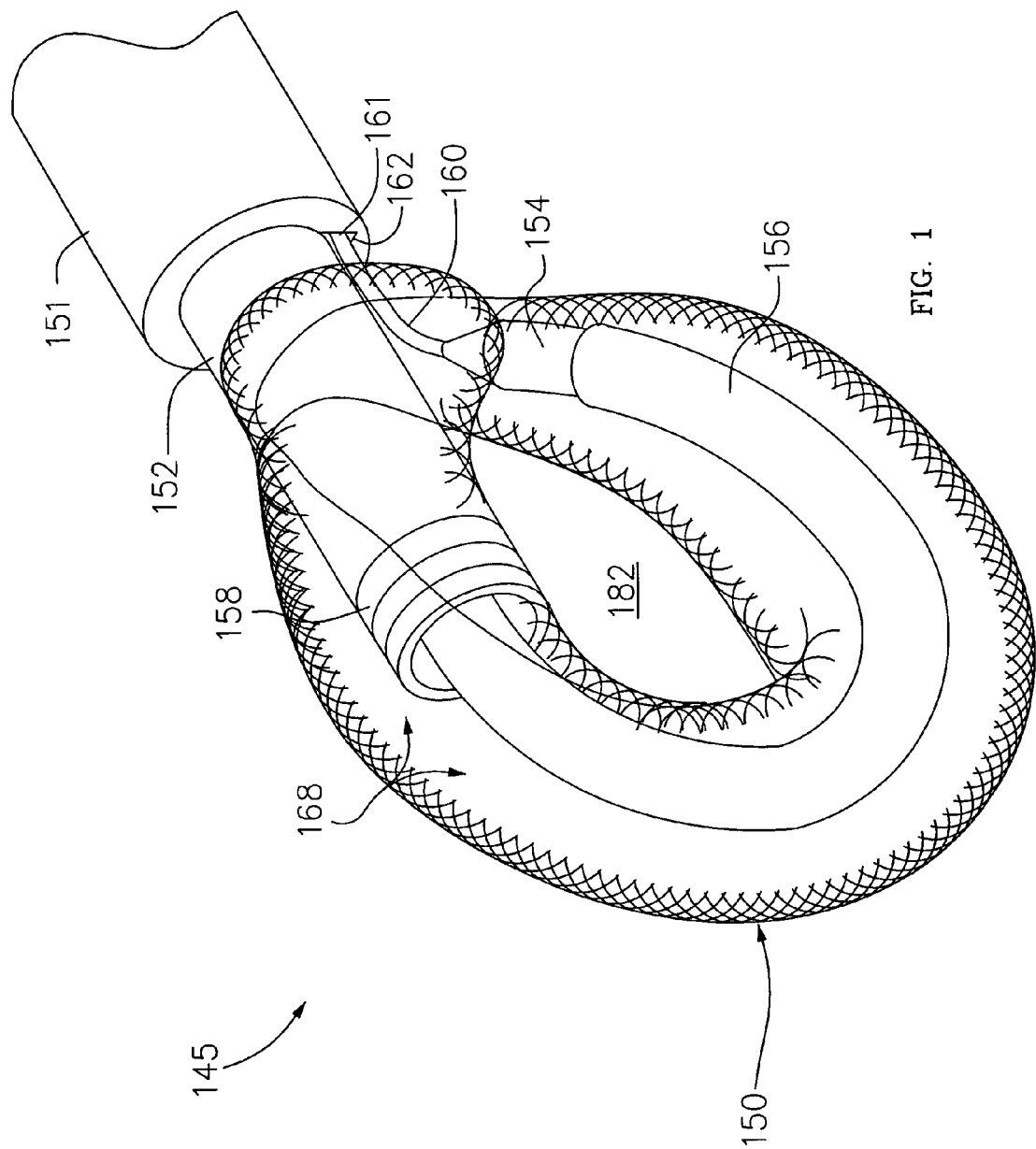
FIG. 1 is a partial sectional view the present invention showing the expandable mesh with the threaded nut attachment means to a delivery tubular member, with the injection tubular member coaxially associated within the delivery tubular member and an introducer tubular member coaxially associated within the injection tubular member and a guiding member coaxially associated within the introducer tubular member, and the distal end of the guiding member engaged to the delivery tubular member by a collet tubular member.

FIG. 1 shows a partial sectional view the present invention 145 showing the unfilled expandable mesh or loop 150 with threaded nut attachment means 158 that functions to removably engage a delivery tubular member 152. An injection tubular member 156 is coaxially associated within the delivery tubular member 152. Coaxially within the injection tubular member 156 is an introducer tubular member 154. Coaxially associated within the introducer tubular member 154 is a guiding member 160. The distal end 162 of the guiding member 160 is engaged between the delivery tubular member 152 and the collet tubular member 151. Not shown in FIG. 1 but shown and explained in more detail in FIG. 9, the present invention consists of an elongated catheter body with a proximal end and a distal end.

Near the distal end of the elongated catheter, is situated an expandable, braided, woven, knitted or embroidered substantially tubular loop 150 in an unfilled (pre-delivery or pre-injection of one or more materials) configuration. The distal end of one end of the expandable mesh or loop is fed into the proximal end, of the other end of the expandable mesh or loop in a manner similar to a snake eating its own tail (with overlapping section). This design results in an expandable mesh 150 having a toroidal configuration with an inner chamber 168 and inside open central area 182. Also this design results in an overlapping section 170 whereby a screw thread attachment means 172a and 172b are designed to removable engage the delivery tube member 152 (shown in more detail in FIGS. 10, 11, 12, and 13).

The expandable mesh 150 is fabricated as a knit, weave or braid and can be constructed from non-degradable materials. Suitable non-degradable materials for the expansile loop 150, include, but are not limited to, polyetheretherketone (PEEK), Nylon, Dacron, synthetic polyamide, polypropylene, expanded polytetrafluroethylene (e-PTFE), polyethylene, polyolefin (e.g. heat shrink tubing, Teflon (PTFE), polyurethane, Pebax, Hytrel, and ultra-high molecular weight fibers of polyethylene (UHMWPE) commercially available as Spectra™ or Dyneema™, as well as other high tensile strength materials such as Vectran™, Kevlar™, natural or artificially produced silk and commercially available suture materials used in a variety of surgical procedures. The expandable mesh 150 is fabricated as a weave knit or braid and can be constructed from biodegradable or bioabsorbable materials. Suitable biodegradable and bioabsorbable materials for the expandable mesh 150 include, but are not limited to, resorbable collagen, LPLA (poly(l-lactide)), DLPLA (poly(dl-lactide)), LPLA-DLPLA, PGA (polyglycolide), PGA-LPLA or PGA-DLPLA, and biodegradable sutures made from polylactic acid, polyglycolic acid, and polycaprol acetone.

In addition, for some embodiments, suitable metallic materials for the expansile loop 150 may be used that include, but are not limited to, stainless steel, cobalt-chrome alloy, titanium, titanium alloy, or nickel-titanium shape memory alloys, among others. It is further contemplated that the metallic mesh can be interwoven with non-resorbable polymers such as nylon fibers, polypropylene fibers, carbon fibers and polyethylene fibers, among others, to form a metal-polymer composite weave. Further examples of suitable non-resorbable materials include DACRON and GORE-TEX. One feature of the expandable mesh or loop 150 is that it needs to have pore sizes or openings that are small enough to hold the filling material or nucleus from extruding out and large enough to maintain flexibility and expansion characteristics.

Shown in FIG. 2 is a side view of the guide wire member 160. Guide wire member 160 is preferable fabricated from Nitinol™ but or suitable metallic materials include, but are not limited to, stainless steel, cobalt-chrome alloy, titanium, titanium alloy, or nickel-titanium shape memory alloys, among others. It is also anticipated by the Applicants that suitable polymeric materials or braided suture could be suitable as the fabrication material of the guide wire member 160. The guide wire member 160 generally has an outside diameter in the range of 0.003" to 0.030", and preferably between 0.010" and 0.025". The outside diameter of the guide wire member 160 must by small enough in diameter to be coaxially associated with the inside lumen diameter of the introducer tubular member 154.

Shown in FIG. 3 is a side view of the introducer tubular member 154. The introducer tubular member 154 is fabricated generally as a tubular structure. Suitable materials for the introducer tubular member 154, include, but are not limited to, polyetheretherketone (PEEK), Nylon, Dacron, synthetic polyamide, polypropylene, polyolefin, Teflon (PTFE), polyurethane, Pebax, Hytrel, expanded polytetrafluoroethylene (e-PTFE), polyethylene and ultra-high molecular weight fibers of polyethylene (UHMWPE) commercially available as Spectra™ or Dyneema™, as well as other high tensile strength materials such as Vectran™, or Kevlar™. The introducer tubular member 154 generally has an outside diameter in the range of 0.013" to 0.098", and preferably between 0.090" and 0.095". Its wall thickness is typical for its diameter and generally is in the range of 0.0015" to 0.045" and preferably between 0.025" and 0.035" thereby having an inner lumen diameter in the range of 0.005 to 0.033, and a preferred inner lumen diameter in the range of 0.013 to 0.028. The outside diameter of the introducer tubular member 154 must be small enough to allow coaxial association with the inside lumen diameter of the injection tubular member 156. The distal end of the introducer tubular member 156 can be tapered to facilitate movement over the guiding member 160 inside the expandable mesh/loop.

Shown in FIG. 4 is a side view of the injection tubular member 156. The injection tubular member 156 is fabricated generally as a tubular structure. Suitable materials for the injection tubular member 156, include, but are not limited to, PEEK (polyetheretherketone), Nylon, Dacron, synthetic polyamide, polypropylene, polyolefin (e.g. heat shrink tubing), Teflon (PTFE), expanded polytetrafluroethylene (e-PTFE), polyetheretherketone (PEEK), polyurethane, Pebax, Hytrel, polyethylene and ultra-high molecular weight fibers of polyethylene (UHMWPE) commercially available as Spectra™ or Dyneema™, as well as other high tensile strength materials such as Vectran™, or Kevlar™. The outer tubular member of the injection tubular member 156 generally has an outside diameter in the range of 0.033" to 0.143", and preferably between 0.120" and 0.130". Its wall thickness is typical for its diameter and generally is in the range of 0.010" to 0.040" and preferably between 0.015" and 0.025" thereby having an inner lumen diameter in the range of 0.080" to 0.110", and a preferred inner lumen diameter in the range of 0.090" to 0.100". The outside diameter of the injection tubular member 156 must be small enough to allow coaxial association with the delivery tubular member 152. In addition, the injection tubular member is designed to bend around the expandable mesh/loop radial diameter without kinking or crushing. It wall construction could contain a polymer inner jacket or a braid or coil middle layer and a polymer outer jacket. The injection tubular member is designed to bend around the radius of the inner expandable mesh/loop without kinking or crushing. Its construction could also include an inner jacket or braided coil middle layer with a polymer outer jacket. Attached to the proximal end of the injection tubular member is a connection means 164. The connection means 164 is a typical screw type connection that is designed to removably engage an injection mechanism that utilizes a delivery means e.g. air pressure, mechanical pressure, electro-mechanical pressure, hydrodynamic pressure, as shown in FIGS. 24-27, and/or vibratory or oscillatory energy (not shown).

Shown FIG. 5 is a side view of the delivery tubular member 152. The delivery tubular member 152 is fabricated generally as a tubular structure. Delivery tubular member 152 is preferable fabricated from suitable metallic materials that include, but are not limited to, stainless steel, cobalt-chrome alloy, titanium, titanium alloy, or nickel-titanium shape memory alloys, among others. Other suitable materials for the delivery tubular member 152, include, but are not limited to, Nylon, Dacron, polyetheretherketone (PEEK), synthetic polyamide, polypropylene, expanded polytetrafluoroethylene (e-PTFE), polyethylene, polyolefin (e.g. heat shrink tubing), Teflon (PTFE), Ultem, Polycarbonate, polysulfone, polyurethane, Pebax, Hytrel, Acetal and ultra-high molecular weight polyethylene (UHMWPE) commercially available as Spectra™ or Dyneema™, as well as other high tensile strength materials such as Vectran™, or Kevlar™. The outer tubular member of the delivery tubular member 152 generally has an outside diameter in the range of 0.140" to 0.190", and preferably between 0.160" and 0.170". Its wall thickness is typical for its diameter and generally is in the range of 0.005" to 0.025" and preferably between 0.010" and 0.020" thereby having an inner lumen diameter in the range of 0.120 to 0.150, and a preferred inner lumen diameter in the range of 0.130 to 0.140. The outside diameter of the delivery tubular member 152 must be small enough to allow close coaxial association with the collet tubular member 151. One unique feature of the delivery tubular member 152 is that at the distal end the of this member is a flattened section 166 (shown in more detail in FIGS. 5 and 8) which is designed to receive the distal end of the guide wire member 160 which is fixedly engaged when the collet tubular member 151 slides over and is located within the flattened distal section 166. When the collet tubular member 151 is retracted proximally past the flattened section 166, the guide wire member 160 is no longer fixedly engaged between the flattened section 166 and the collet tubular member 151 therefore can be retracted and removed during the delivery and injection procedure. It is anticipated by the Applicants that another engagement means can be employed, such as press fit design, whereby the collet tubular member 151 may not be a necessary component of the system.

Shown in FIG. 6 is a side view of the collet tubular member 151. Collet tubular member 151 is preferable fabricated from suitable metallic materials that include, but are not limited to, stainless steel, cobalt-chrome alloy, titanium, titanium alloy, or nickel-titanium shape memory alloys, among others. Other suitable materials for the collet tubular member 151, include, but are not limited to, polyetheretherketone (PEEK), Nylon, Dacron, synthetic polyamide, polypropylene, expanded polytetrafluroethylene (e-PTFE), polyethylene, polyolefin (e.g. heat shrink tubing), Teflon (PTFE), polyurethane, Ultem, polysulfone, polycarbonate, and ultra-high molecular weight polyethylene (UHMWPE) commercially available as Spectra™ or Dyneema™, as well as other high tensile strength materials such as Vectran™, or Kevlar™. The collet tubular member 151 generally has an outside diameter in the range of 0.178" to 0.218", and preferably between 0.198" and 0.208". Its wall thickness is typical for its diameter and generally is in the range of 0.002" to 0.025" and preferably between 0.005" and 0.020" thereby having an inner lumen diameter in the range of 0.158" to 0.188", and a preferred inner lumen diameter in the range of 0.168 to 0.178. The inside diameter of the collet tubular member 151 must be small enough to allow close coaxial association with outside diameter of the delivery tubular member 152 so that when guide wire member 160 is engaged between the flattened section 166 and the collet tubular member 151 it becomes engaged by physical contact. When the collet tubular member 151 is retracted proximally past the flattened section 166, the guide wire member 160 is no longer fixedly engaged and can be retracted and removed during the delivery and injection procedure.

FIG. 7 is a cross-sectional view of the delivery tubular member 152 in FIG. 5 showing a distally positioned flattened section 166 whereby the guiding member 160 is physically engaged by the collet tubular member 151. Retracting the collet tubular member 151 proximally releases physical engagement of the guiding member 160. Once the collet tubular member 151 is retracted, the guiding member 160 can be fully retracted and removed. It is anticipated by the Applicants that the guiding member 160 can be removably engaged to the delivery tubular member 152 by another engage means (e.g. removable press fit) whereby the collet tubular member 151 would not be required as a component of the present invention.

FIG. 8 is a side view of expanded distal section view of FIG. 5 further showing the distally position flattened section 166 which is designed to provide a engagement base for the guiding member to be physically attached by engagement with collet tubular member 151.

FIG. 9 is a side view of the present invention 145 showing the expandable mesh 150, the collet tubular member 151, the delivery tubular member 152, the injection tubular member 156 and the guiding member 160. As previously described, the guiding member 160 is in coaxial association with the introducer tubular member 154, the introducer tubular member 154 is in coaxial association with the injection tubular member 156, the injection tubular member 156 is in coaxial association with the delivery tubular member 152, and the delivery tubular member 152 is in coaxial association with the collet tubular member 151. Removably attached to the distal end of the delivery tubular member 154 is the expandable mesh 150.

Figure 10:
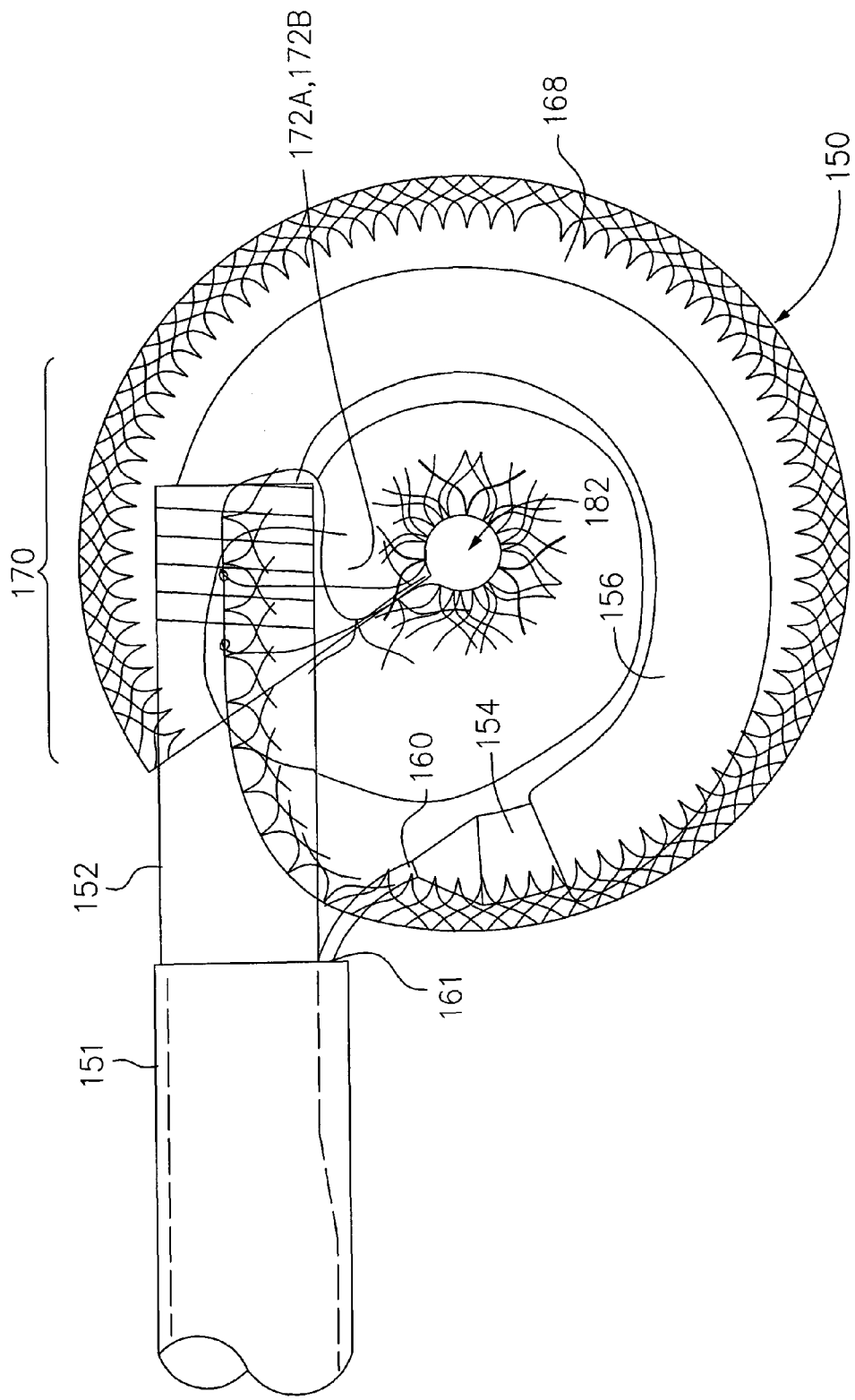
FIG. 10 is a partial cross-section view of the distal end of the present invention showing in more detail the threaded nut attachment means and self-sealing section.
Figure 11:
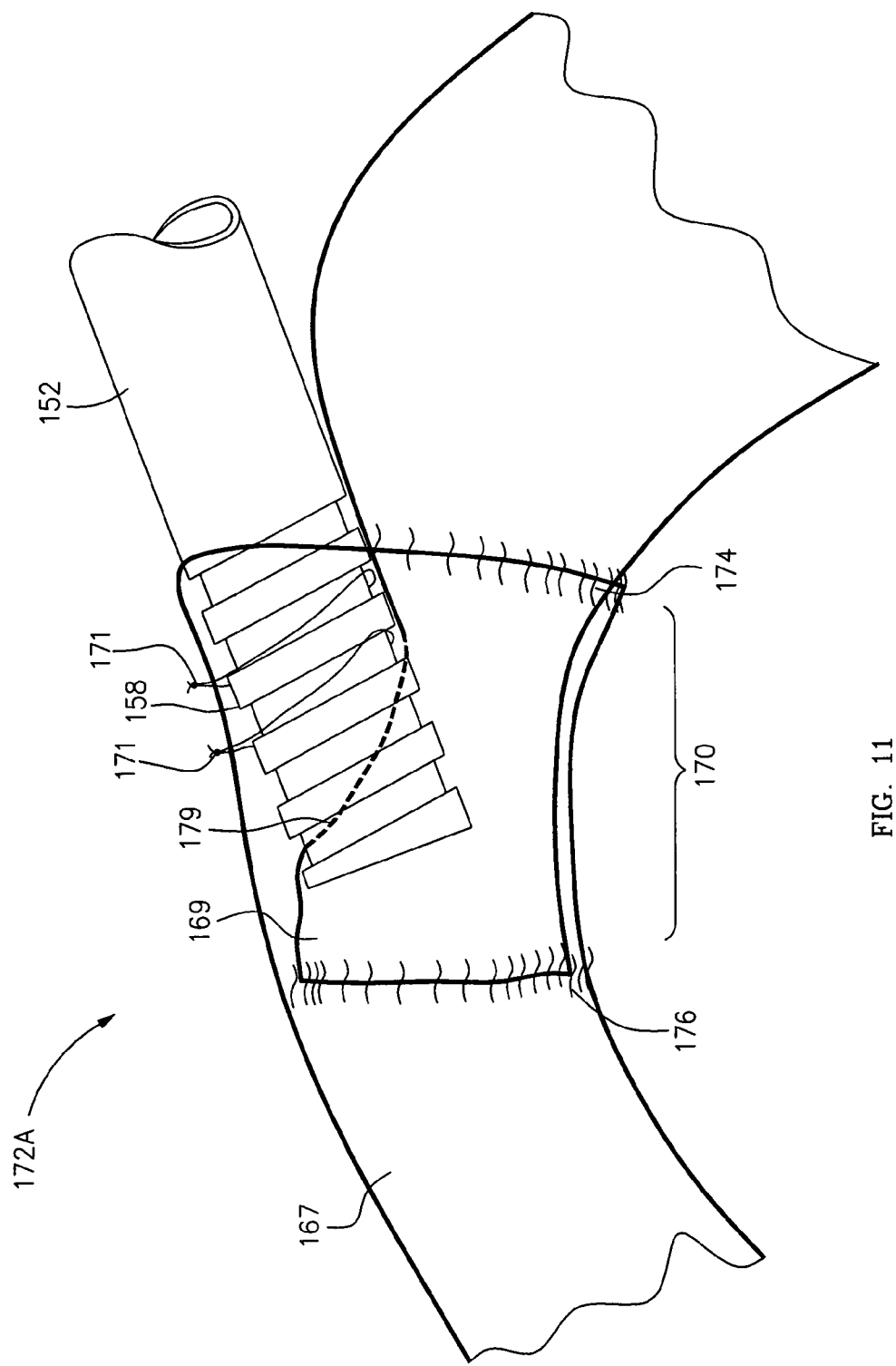
FIG. 11 is a partially sectional side view of the expandable mesh overlapping area showing a first embodiment of the self-sealing design.

FIG. 10 is a partial cross-section view of the distal end of the present invention showing in more detail the threaded nut attachment and self-sealing section. Within the overlapping area 170 of the expandable mesh 150 a thread "nut" 171 made of sutures is installed on the inside surface that joins the inner and outer overlapping mesh ends. The threaded "nut" section 171 has proximal and distal threaded sections which are designed to screwably engage the screw threaded area located on the distal end of the delivery tubular member 152 (shown in detail in FIG. 8). Described her are two different threaded "nut" designs 171 although is anticipated by the Applicants that another nut designs configuration. In one embodiment shown in more detail in FIG. 11, the proximal threaded "nut" section has suture type materials that is sewn in a "270 degree" pattern around the inside surface of the first overlapping section 170 (see FIG. 11). The "270 degree pattern" is used to define that the sewn threaded section does not encircle the entire circumference of the substantially tubular mesh configuration but rather refers to a partial encirclement that allows a tubular member to pass through the sewn threaded section. The actual circular sewn threaded section can range from approximately 50 to 300 degrees around the circumference. The distal threaded "nut" section has suture material that is sewn in a "360 degree pattern" around the inside surface of the second overlapping section 170 resulting in a first threaded "nut" section 172a (see FIG. 11). The "360 degree pattern" is used to define that the sewn threaded section does substantially encircle the entire circumference of the substantially tubular mesh configuration. The actual circular sewn threaded section can range from approximately 360 to 260 degrees around the circumference. The distal screw threaded end of the delivery tubular member enters the inner chamber 168 of the expandable mesh through an opening (179) inside tubular mesh within the inner overlapping mesh section 170. The coaxially associated injection tubular member, introducer tubular member and the guiding member all enter through this opening into the mesh inner chamber 168.

Figure 12:
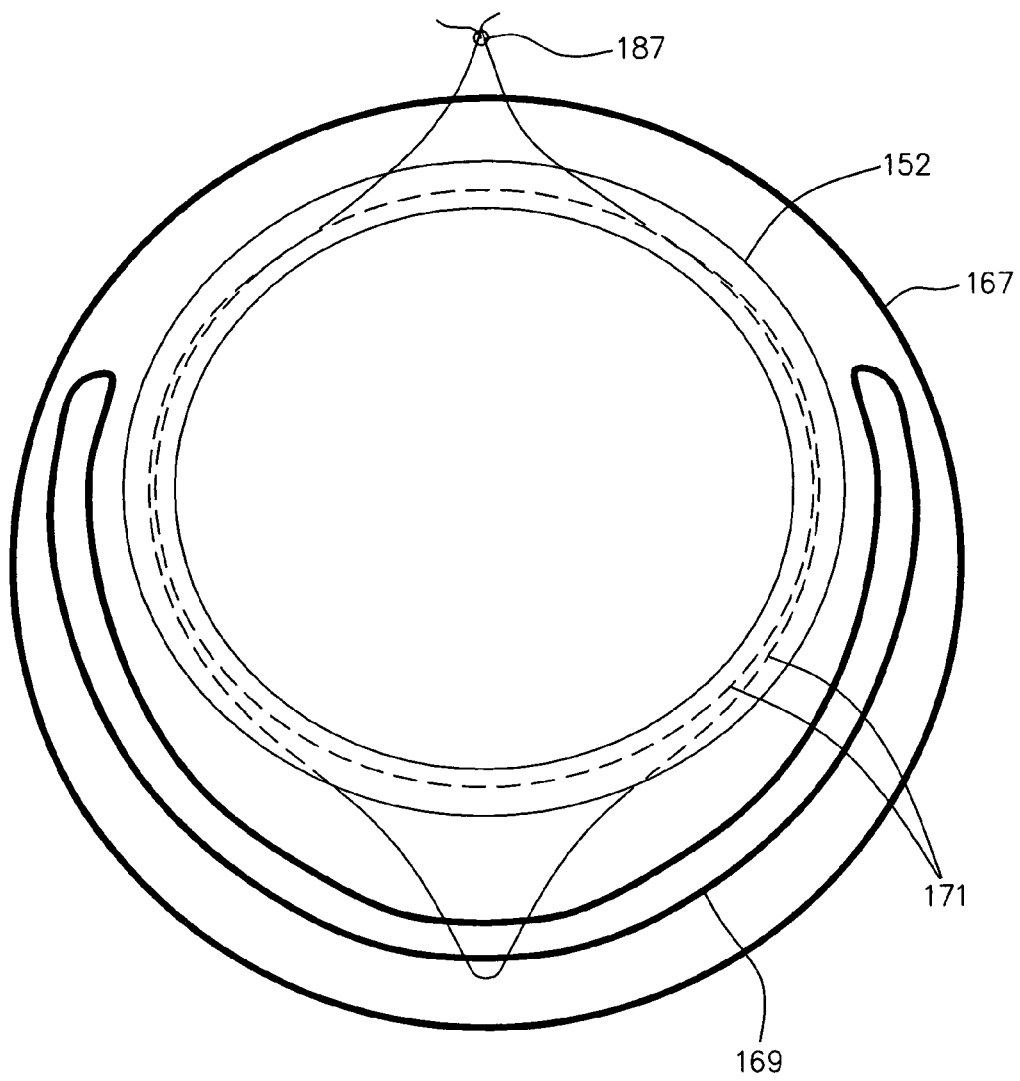
FIG. 12 is a cross section view of and inner mesh section over lapping an outer mesh section and further showing the threaded nut means.
Figure 13:
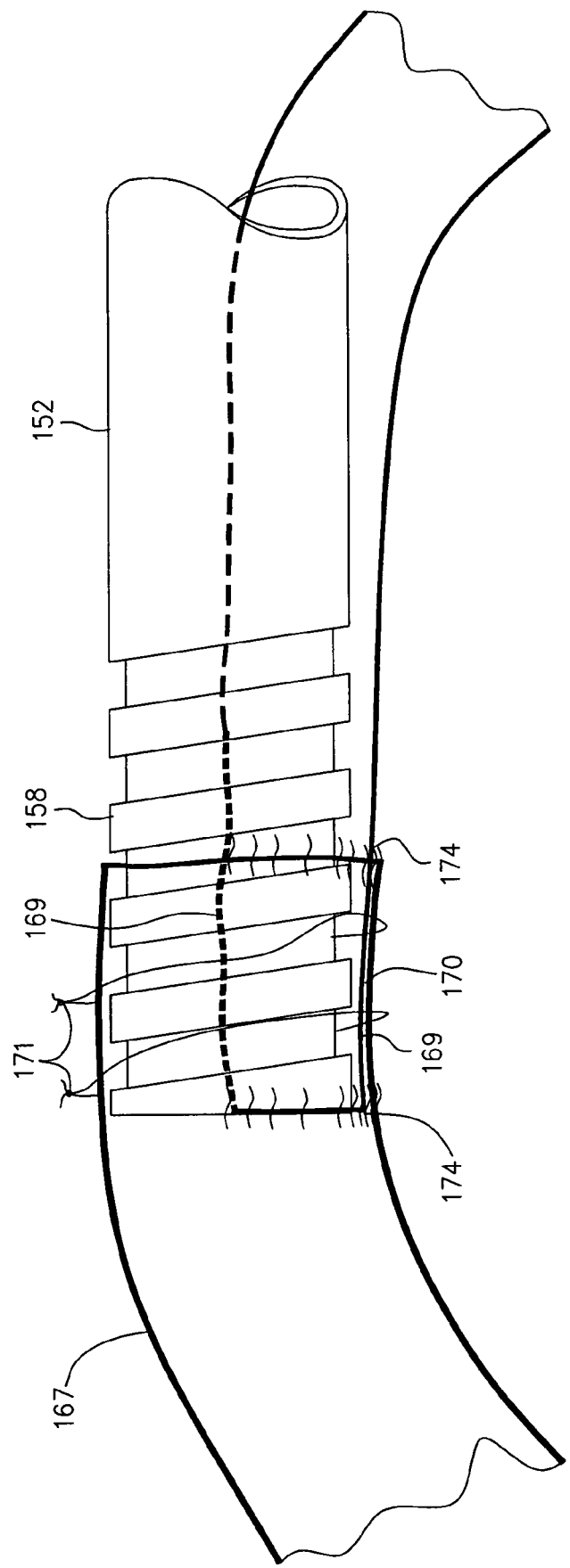
FIG. 13 is a partially sectional side view of the expandable mesh overlapping area showing a second embodiment of the self-sealing design.

FIG. 12 is a cross section view of and inner mesh section 169 over lapping area 170 an outer mesh section 167. The distal section of the delivery tubular member 152 is revomable from the expandable mesh/loop by engaged the suture threaded nut 171 that circles the circumstance of the lapping area 170 it least one time. The two sutures of the threaded nut 171 are shown to be knotted together 187.

In the other embodiment (shown in FIG. 13), the proximal threaded "nut" section has sutures that are sewn in a 270 degree pattern around the inside surface of the first overlapping section 170. The distal threaded "nut" section has sutures that are also sewn in a 270 degree pattern around the inside surface of the second overlapping section 170 resulting in a second threaded "nut" section 172b. The distal screw threaded end of the delivery tubular member enters the inner chamber 168 of the expandable mesh in a channel or pouch 178 between the inner overlapping mesh and the outer overlapping mesh. The coaxially associated injection tubular member, introducer tubular member and the guiding member all enter through this pouch area 178 into the mesh inner chamber 168. In either embodiments, when the delivery tubular member 152 is unscrewed from the threaded "nut" section, the overlapping section 170 functions to self-seal the opening in the mesh 150, preventing the extrusion of injected materials 180 from the inner chamber 168. As material is injecting into the mesh inner chamber 168 or the central area pressure is applied to the overlapping area 170 further sealing the opening. The overlapping area 170 functions similar to a standard flap valve or duck bill valve in that as internal pressure increase two segments engage to create a sealing. Furthermore, the design of the braided expandable mesh also provides for sealing capabilities as when an object, such as the delivery tubular member 152, is removed, the braided fibers re-align themselves to close the hole.

Figure 14:
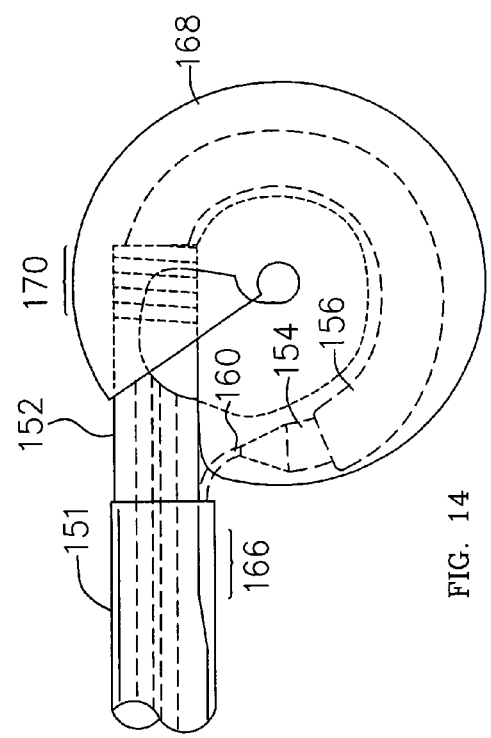
FIG. 14 is a cross-sectional of the present invention with introducer tubular member and injection tubular member advanced over the guiding member within the expandable mesh loop and showing the location of the guiding member within the introducer tubular member.

In typical clinical use, the nucleus of the damaged disc has been previously removed by discectomy techniques either through an anterior, posterior, posterolateral or lateral surgical approach. The expandable mesh 150 in a compressed configuration within an outer catheter element or sheath and is advanced through an access tube or cannula previously placed into the inter-vertebral space. This cannula may access the inter-vertebral space from a lateral, posterior, posterolateral or anterior approach that is well known to physicians skilled in the art. The expandable mesh is then advanced into the inter-vertebral space through the access tube. As shown in FIG. 14, the combination of the introducer tubular member 154 and the guiding member 160 facilitates the injection tubular member 156 to functionally encircle the radius of the mesh inner chamber 168. In addition, (but not shown in FIG. 14) the functionally combination of the introducer tubular member 154, the guiding member 160, and the injection tubular member 156 assists the expandable mesh to extend within the inner annular area or within the inter-vertebral space prior to injection or delivery any materials into the mesh inner chamber 168.

Figure 15:
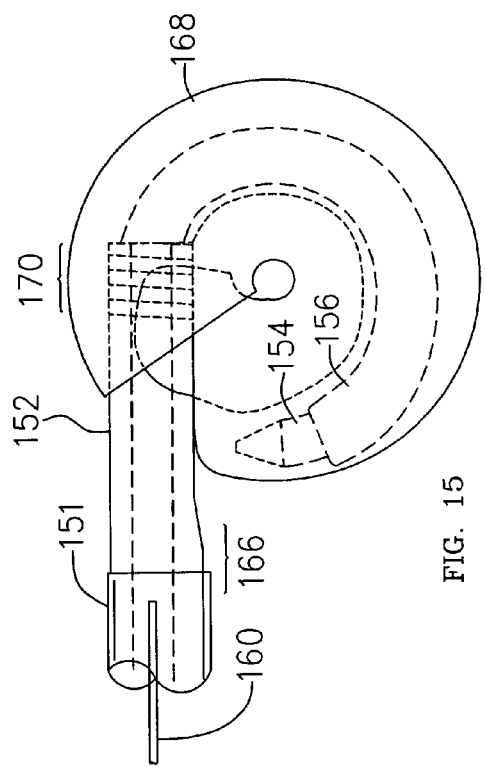
FIG. 15 is a cross-section view of the present invention with the collet member proximally retracted and the guiding member removed.
Figure 16:
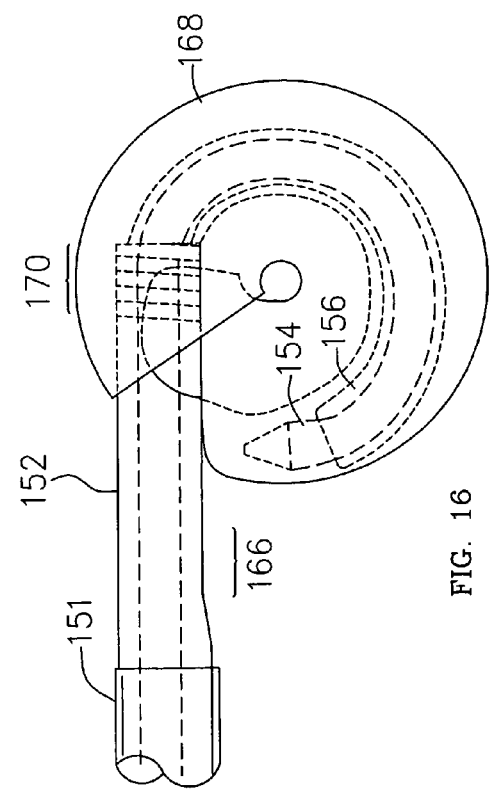
FIG. 16 is a cross-section view of the present invention with the collet member proximally retracted and the guiding member removed and showing the location of the introducer tubular member within the injection tubular member.
Figure 17:
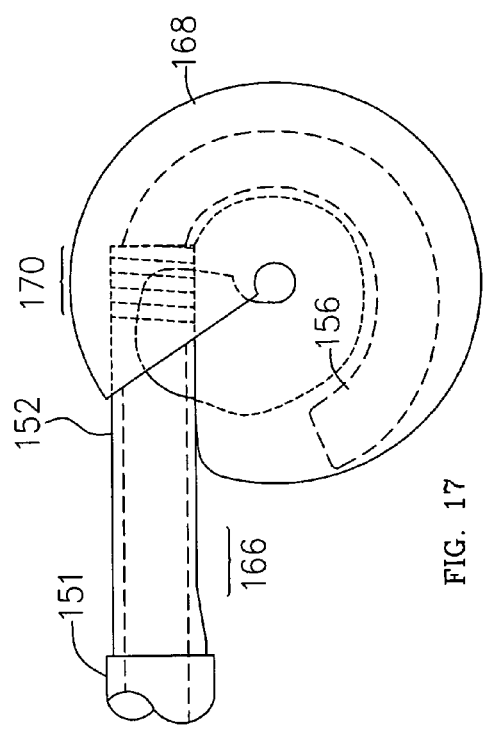
FIG. 17 is a cross-sectional view of the present invention showing the introducer tubular member retracted and the injection tubular member in position for delivery of an injectable material.

Once the expandable mesh 150 is delivered into the inter-vertebral space, the collet tubular member 151 is partially proximately located as shown in FIG. 14. When the collet tubular member 151 is retracted proximally past the flattened section 166 (see FIG. 15), the guide wire member 160 is no longer fixedly engaged and can be retracted and removed to be located proximally with the delivery tubular member 152. It is anticipated by the Applicants that the guiding member 160 can be removably engaged to the delivery tubular member 152 by another attachment means (e.g. removable press fit) whereby the collet tubular member 151 would not be required as a component of the present invention. As shown in FIG. 16, once the guiding member 160 is removed, the introducer tubular member 154 and injection tubular member 156 remain in the encircle radius configuration within the inner chamber 168 of the expandable mesh 150. It is anticipated by the Applicants that the guiding member 160 and the introducer tubular member 154 can be removed simultaneously. In either method the result is, as shown in FIG. 17, with the introducer tubular member 154 and the guiding member 160 retracted, that the injection tubular member 156 is in position for delivery of an injectable material 180. An injection mechanism can now be connected to the proximal connector 164 of the injection tubular member 156 to facilitate delivery of the injection material 180.

Figure 18:
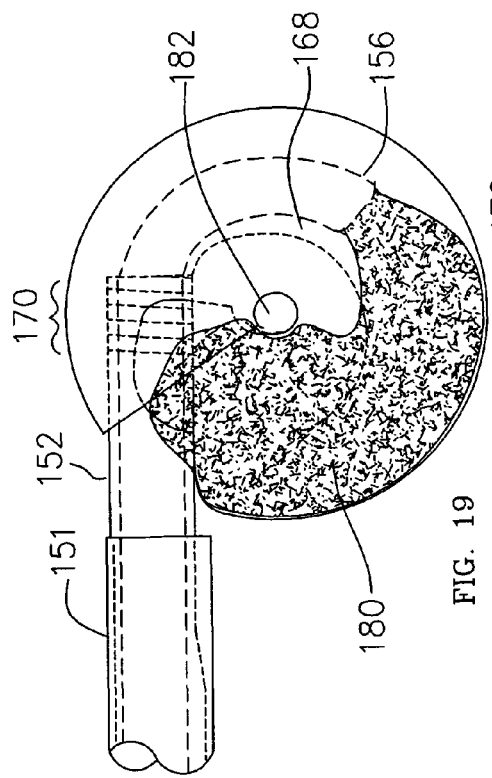
FIG. 18 is a partial sectional side view of the present invention showing a material being initially injected into the inner chamber of the substantially tubular expandable mesh.

As shown in FIG. 18, the injection tubular member 156 is in a first extended position for initially injecting the injectable materials 180 into the inner chamber 168 of the substantially tubular expandable mesh 150. Injectable materials 180 which may be injected include biocompatible viscoelastic materials such as hydrophilic polymers, hydrogels, homopolymer hydrogels, copolymer hydrogels, multi-polymer hydrogels, or interpenetrating hydrogels, acrylonitrile, acrylic acid, acrylimide, acrylimidine, including but not limited to PVA, PVP, PHEMA, PNVP, polyacrylainides, poly(ethylene oxide), polyvinyl alcohol, polyarylonitrile, and polyvinyl pyrrolidone, silicone, polyurethanes, polycarbonate-polyurethane (e.g., Corethane) other biocompatibile polymers, or combinations thereof. The injected biocompatible material may cure or polymerize in situ within the expandable mesh 150 within the disc space. Such in situ curing of the biocompatible material may be the result of mixing of multiple components and polymerization, temperature change in going from room to body temperature or elevated to body temperature, or other forms of energy such as light or electricity applied to the injected material.

In addition to the materials disclosed, additional suitable fluid materials for nucleus replacement include, but are not limited to, various pharmaceuticals (steroids, antibiotics, tissue necrosis factor alpha or its antagonists, analgesics); growth factors, genes or gene vectors in solution; biologic materials (hyaluronic acid, non-crosslinked collagen, fibrin, liquid fat or oils); synthetic polymers (polyethylene glycol, liquid silicones, synthetic oils); and saline.

Additional materials for the embodiments of the present invention 145 to be delivered into the expandable mesh 150 include certain biocompatible cement and plaster of Paris materials. Cement products employ a binding agent to hold silicone materials or sand and other aggregates together in a hard, stone like mass. Other chemicals can be added to the cement components to affect the curing time and final plasticity of the cement product. Plaster of Paris biomaterials are formed from calcium sulfate and are ideal materials for molding, casting and making various forms. The hardness of the plaster of Paris biomaterials can attain a relatively high hardness (Shore A Hardness of 65+/−5) and can fully harden in 30 minutes or less. Both the biocompatible cement and plaster of Paris materials are desirable candidate materials to be used to deliver and fill within the expansile loop or center hole of the present invention for the fusing two adjacent vertebrae together.

Example of calcium phosphate-based bone substitutes having the necessary characteristics consist of calcium phosphate being a substantially monolithic tetracalcium phosphate ($CA_4(PO_4)_2O$). The calcium phosphate may further comprise surface protrusions of calcium phosphate to enhance bone integration. Alternatively, the suitable calcium phosphate-based bone substitute can comprise minor amounts of additional substances, such as $Na_3PO_4$; $Na_2HPO_4$; $NaH_2PO_4$; $Na_4HPO_4.7H_2O$; $Na_3PO_4.12H_2O$; $H_3PO_4$; $CaSO_4$; $(NH_4)_3PO_4$; $(NH_4)_2HPO_4$; $(NH_4)H_2PO_4$; $(NH_4)_3PO_4.3H_2O$; $NaHCO_3$; $CaCO3$; $Na_2CO_3$; $KH_2PO_4$; $K_2HPO_4$; $K_3PO_4$; $CaF_2:SrF_2$; $Na_2SiF_6$; $Na_2PO_3F$, and the like. The suitable bone substitute can also comprise an amount of one or more active agents suitable to promote bone growth, such as a growth factor, a bone morphology protein, or a pharmaceutical carrier there for. In addition, the expandable mesh 150 can include materials that will act as a scaffold or carrier for delivering biologic medicaments to vertebral tissues. The expansile mesh can be previously treated (for example, by soaking) with certain biologics (e.g. BMP, OP-1), or the access tube can be constructed to include a biologic delivery means such that the biologic is 1) delivered while the injected material 180 is being deployed, 2) delivered prior to deploying the injected material 180, 3) delivery subsequent to deploying the injected material 180, or any combinations thereof.

Furthermore, the present invention expandable mesh 150 can be coated or integrated with an osteogenic paste composition including a paste-form carrier such as a gelatin paste and at least one osteogenic factor such as BMP-2 or another similar bone morphogenetic protein. The inclusion of osteoblast and osteoclast-stimulating osteogenic factors in a paste-form composition including a resorbable paste carrier causes a rapid and premature resorption of the carrier. This rapid resorption of the carrier can diminish or eliminate the capacity of the paste-form composition to effectively stimulate and support new bone formation in a void filled with the composition. This is particularly the case in humans in which the rate of new bone formation is relatively slow.

Other suitable materials to induce bone fusion including, but are not limited to, bond graft materials such as any described "bone cements" or any polymeric bone graft compounds, bone chips, bone graft materials, nylon fibers, carbon fibers, glass fibers, collagen fibers, ceramic fibers, polyethylene fibers, polypropylene fibers, poly(ethylene terephthalate), polyglycolides, polylactides, and combinations thereof, or a biomaterial or any suitable material (as described above), as the present invention is not limited in this respect.

In addition, suitable materials that can be placed directed into the expandable mesh 150 and allowed to expand through the absorption of liquids such as water include, but are not limited to, swelling hydrogel materials (e.g. polyacrliamide, polyacrylonitrile, polyvinyl alcohol or other biocompatible hydrogels). Examples of suitable materials for solid or semi-solid members include solid fibrous collagen or other suitable hard hydrophilic biocompatible material. The swelling of these materials may result in further expansion of the expansile braided, woven or embroidered loop and an increase in the inter-vertebral disc height.

In some cases, a multiphase system may be employed, for example, a combination of solids, fluids or gels may be used. Such materials may create primary and secondary levels of flexibility within the braided, woven embroidered expansile loop and within the inter-vertebral disc space.

Figure 19:
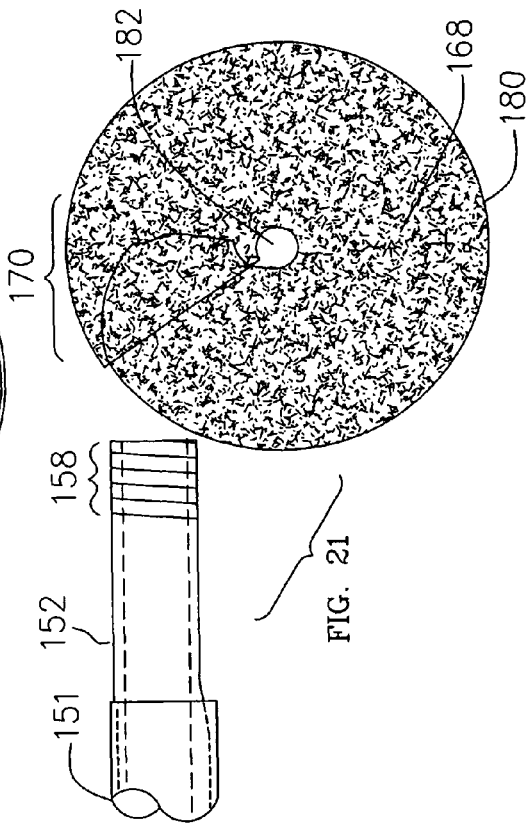
FIG. 19 is a partial sectional side view of the present invention showing the injection tubular member partially retracted as the material is being injected into the inner chamber of the substantially tubular expandable mesh.
Figure 20:
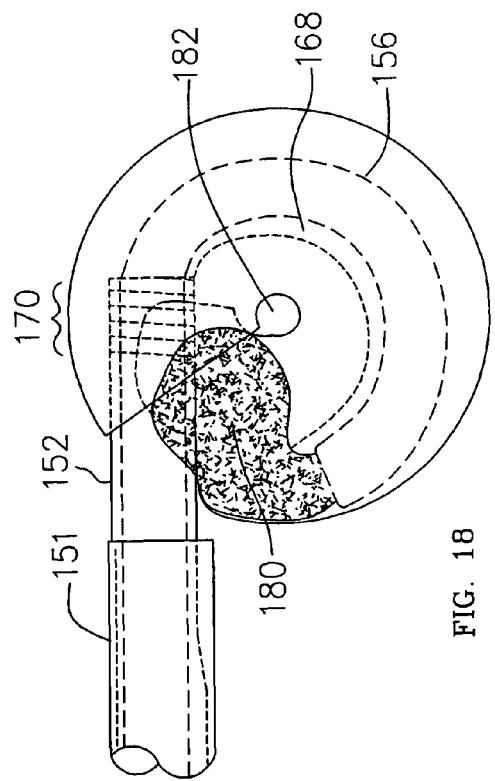
FIG. 20 is a partial sectional side view of the present invention showing the injection tubular member fully retracted and the material fully injected within the inner chamber of the substantially tubular expandable mesh.

For example, the hydrogel materials (e.g. polyacrliamide, polyacrylonitrile, polyvinyl alcohol or other biocompatible hydrogels or combinations can be dissolved in a solvent, such as dimethylsulfoxide, analogues/homologues of dimethylsulfoxide, ethanol, ethyl lactate, acetone, glycerin or combinations thereof. Small amounts of water could also be added to the solvent/hydrogel combination to adjust the solutions viscosity. This solvent/hydrogel combination can be injected into the inter-vertebral space to replace the nucleus, the annulus, or both the nucleus and annulus. The expandable mesh 150 will assist in containing and supporting the solvent/hydrogel combination. After delivery, the solvent is replaced by bodily fluids and the hydrogel precipitates out of solution into a hydrated solid. The solvent is adsorbed into the body tissues. Introducing an aqueous solvent, such as water or saline, into the inter-vertebral space containing the solvent/hydrogel combination can be performed to increase the precipitation speed of the hydrogel. This second step facilitates the precipitation or solidification of the hydrogel material which swells and fills the desired inter-vertebral space. As shown in FIG. 19, the injection tubular member 156 is partially retracted and located in a second extended position as the material is continued to be injected into the inner chamber 168 of the substantially tubular expandable mesh 150. Shown in FIG. 20 the injection tubular member 156 is fully retracted within the delivery tubular member 152 and the material fully injected within the inner chamber 168 of the substantially tubular expandable mesh 150.

Figure 21:
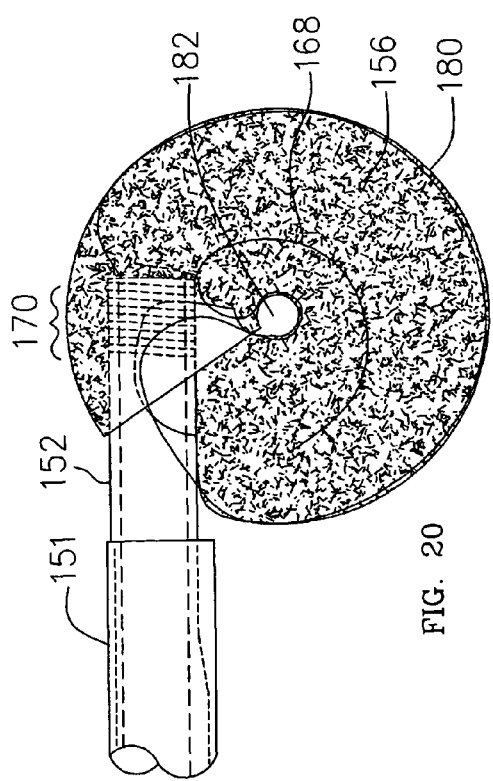
FIG. 21 is a partial sectional side view of the present invention showing the delivery tubular member detached from the fully injected substantially tubular expandable mesh.

Once the expandable mesh 150 is substantially filled with an injectable material 180, as shown in FIG. 21, the delivery tubular member unscrewed from the first threaded "nut" section 172a or the second threaded "nut" section 172b and detached. As shown in FIG. 21, the opening in the overlapping section 170 is self-sealed by the internal pressure of the injected material 180.

Figure 22:
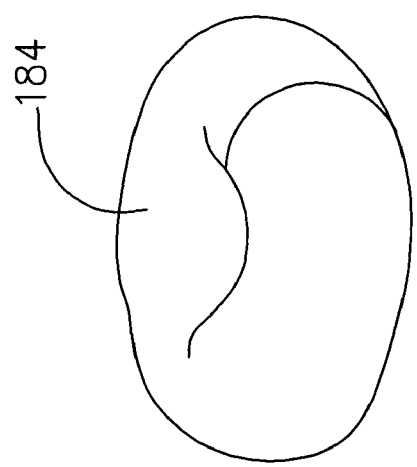
FIG. 22 is a view of the substantially injected tubular expandable mesh.

FIG. 22 is a view of the substantially filled injected tubular expandable mesh 184 fully detached from the delivery components (guiding member 160, introducer tubular member 154, injection tubular member 156, delivery tubular member 152 and collet tubular member 151).

Figure 23:
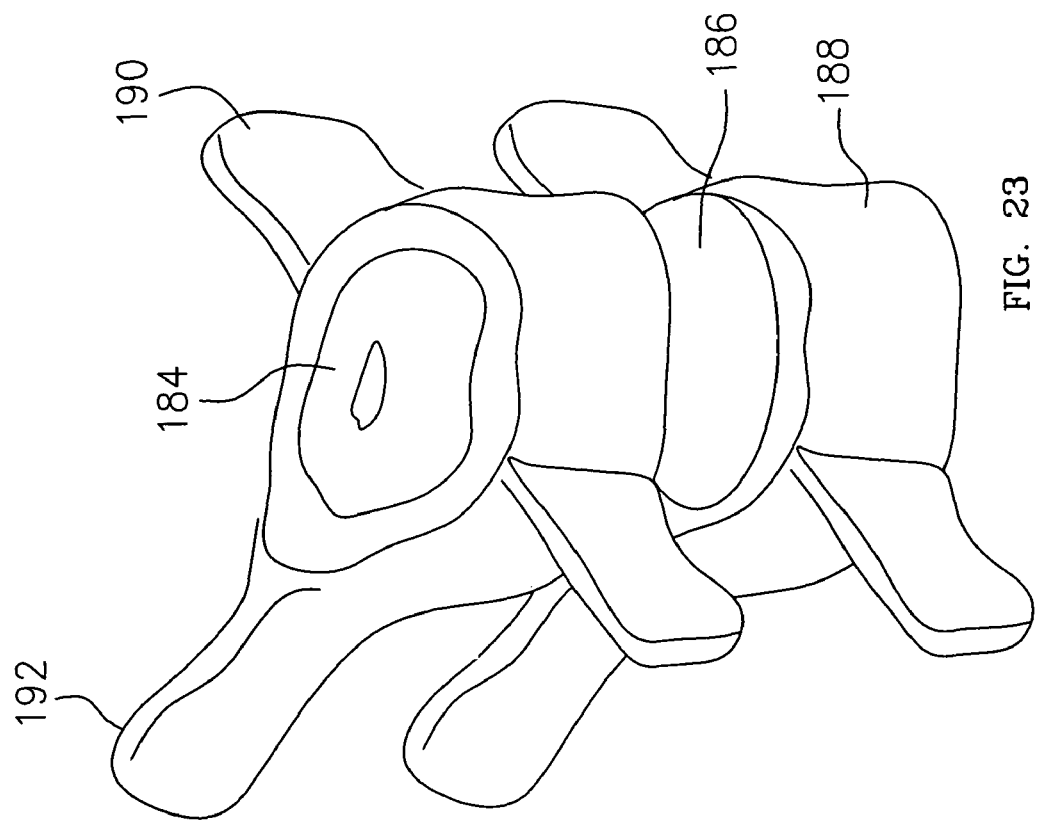
FIG. 23 is a view of the fully injected substantially tubular expandable mesh positioned within a sectional view of the intra-vertebral space of a treated disc.

FIG. 23 is a view of the fully injected substantially tubular expandable mesh 180 positioned within the intra-vertebral space for replacing a damaged vertebral disc. Also shown are other features of the vertebral disk including the pedicles 190 and spinal process 192.

Figure 24:
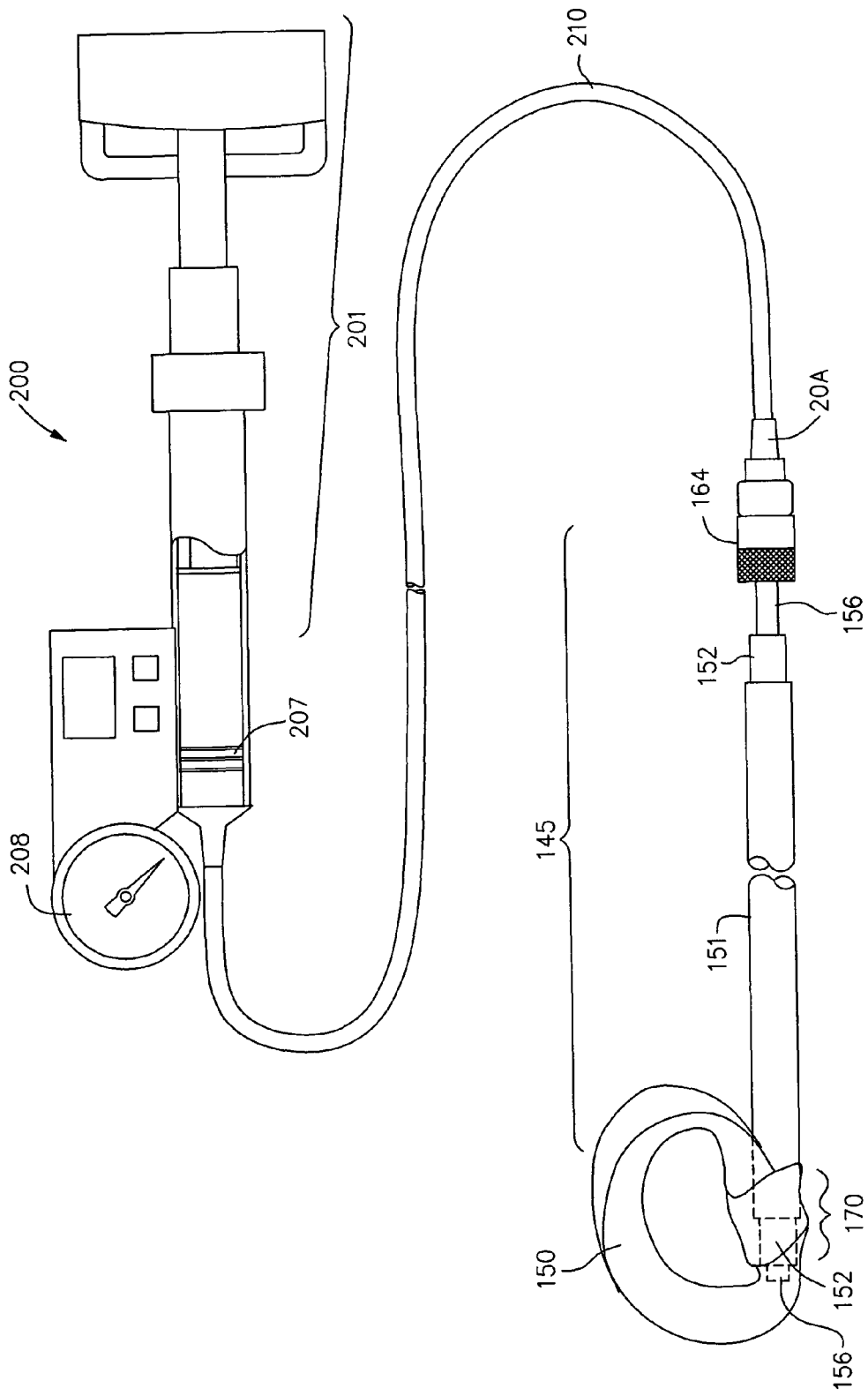
FIG. 24 is a side view of an injection mechanism utilizing an air pressured delivery means and attached to the present invention.

FIG. 24 is an illustration view of an injection mechanism utilizing an air pressure means 200 attached to the present invention 145. In this Figure, the air pressure means is shown as a syringe apparatus or indeflator 201. It is anticipated by the Applicants the various other air pressure producing apparatuses or means can be used in this application. The syringe apparatus of indeflator 201 typically has an airtight plunger 207 and a pressure monitor means 208. The syringe apparatus of indeflator 201 also typically has a connector 209 at the distal end of a length of connection tubing 210 that removable engages the connector means 164 on the injection tubular member 156.

Figure 25:
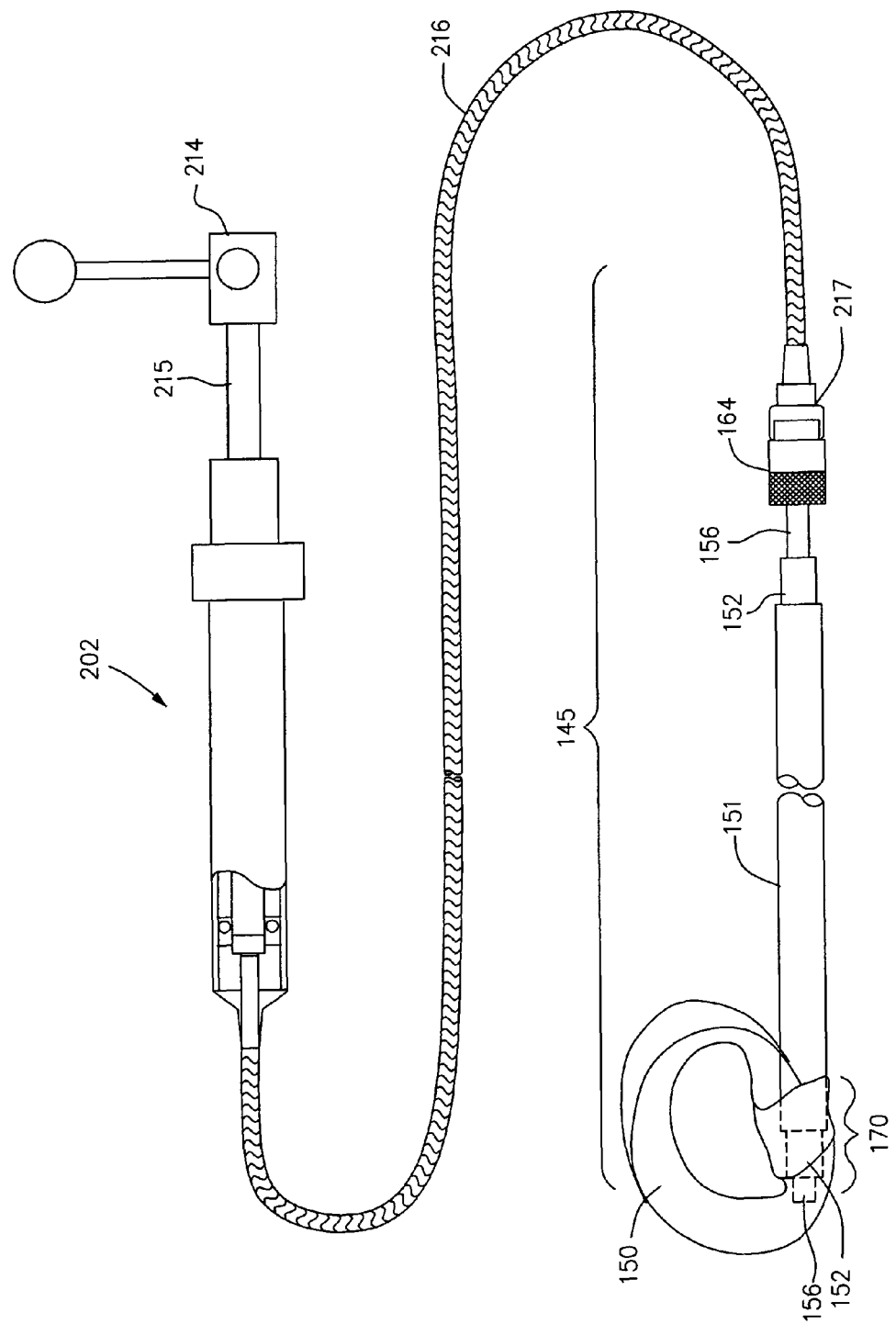
FIG. 25 is a side view of an injection mechanism utilizing a mechanical means and attached to the present invention.

FIG. 25 is an illustration view of an injection mechanism utilizing a mechanical means 202 attached to the present invention 145. The mechanical means 202 typically has a plunger connected with a shaft 215 to a handle mechanism 214. Within the tubing 216 can be a flexible shaft that applies physical pressure from the plunger to the injection material for delivering the material into the expandable mesh. The mechanical means 202 also typically has a connector 217 at the distal end of a length of connection tubing 216 that removable engages the connector means 164 on the injection tubular member 156. It is anticipated by the Applicants the various other mechanical or physical pressing producing apparatuses or means can be used in this application.

Figure 26:
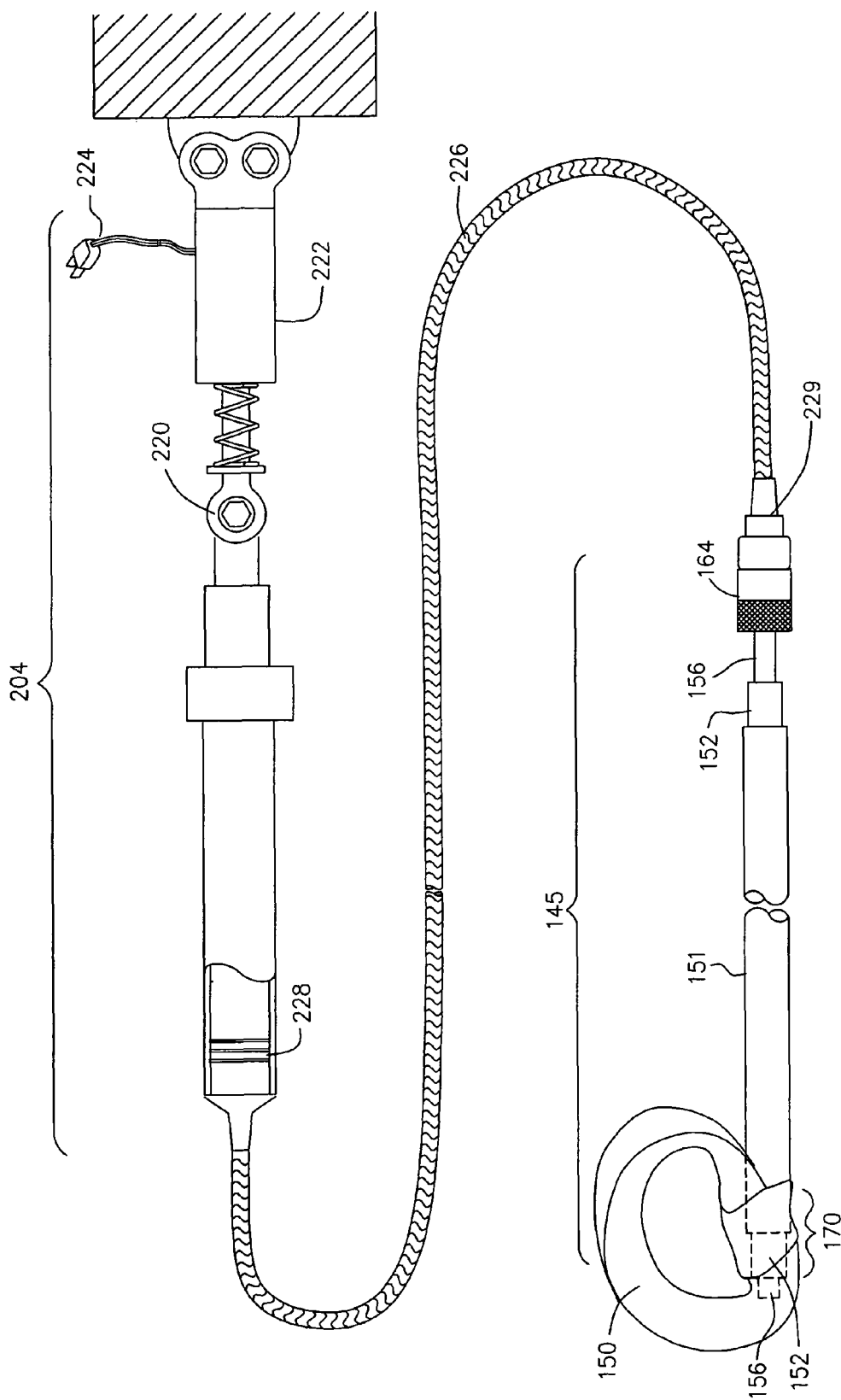
FIG. 26 is a side view of an injection mechanism utilizing an electromechanical means and attached to the present invention.

FIG. 26 is an illustration view of an injection mechanism utilizing an electromechanical means 204 attached to the present invention 145. The mechanical means 204 typically has a plunger connected with a shaft 220 to an electronic advancing mechanism 224. Within the connection tubing 226 can be a flexible shaft that applies physical pressure to the injection material for delivering the material into the expandable mesh. The mechanical means 204 also typically has a connector 229 at the distal end of a tubing 226 that removable engages the connector means 164 on the injection tubular member 156. It is anticipated by the Applicants the various other mechanical or physical pressing producing apparatuses or means can be used in this application.

Figure 27:
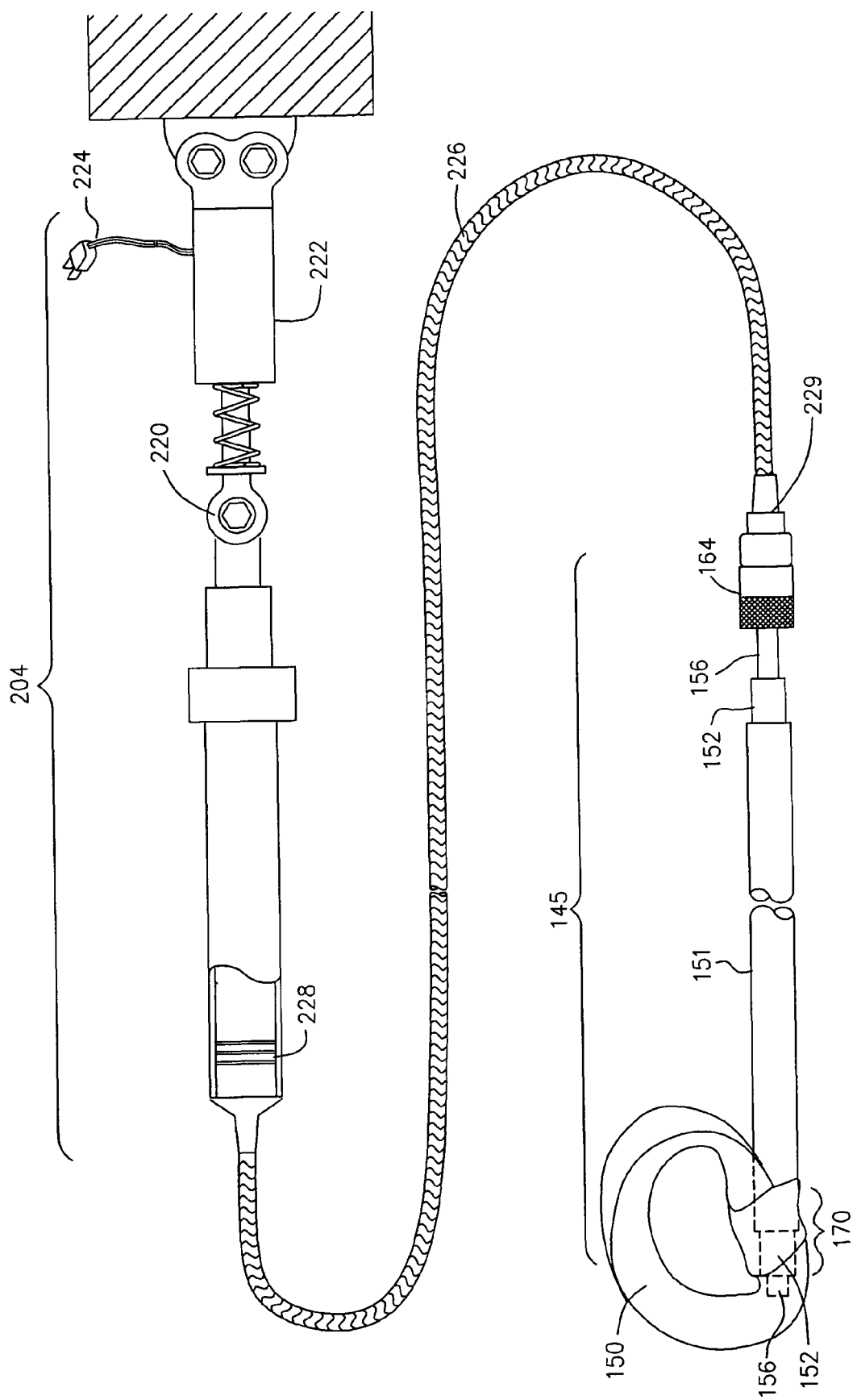
FIG. 27 side view of an injection mechanism utilizing a hydrodynamic means and attached to the present invention.

FIG. 27 is an illustration view of an injection mechanism utilizing a hydrodynamic means 206 attached to the present invention 145. In this Figure, the hydrodynamic means is shown as a syringe apparatus or indeflator 206 using a liquid for applying the pressure. The syringe apparatus of indeflator 231 typically has a liquid-tight plunger 238, a pressure monitor means 232, and may have a liquid reservoir 230. The syringe apparatus of indeflator 231 also typically has a connector 237 at the distal end of a length of connection tubing 234 that removable engages the connector means 164 on the injection tubular member 156. It is anticipated by the Applicants the various other hydrodynamic apparatuses or means can be used in this application.

It should be understood that the foregoing description of the present invention is intended merely to be illustrative thereof and that other embodiments, modifications, and equivalents of the invention are within the scope of the invention recited in the claims appended hereto. Further, although each embodiment described above includes certain features, the invention is not limited in this respect. Thus, one or more of the above-described or other features of the invention, method of delivery, or injection of biomaterial may be employed singularly or in any suitable combination, as the present invention is not limited to a specific embodiment.

The invention claimed is:

1. An apparatus for treating a spinal disc comprising:
   a flexible and expandable braided, woven, knitted or embroidered mesh, said mesh having an inner mesh section in slidable and coaxial cooperation with an outer mesh section, said braided mesh further having an interior chamber and an inner section; a portion of said inner mesh section overlaps within said outer mesh section resulting in a overlapping area, said overlapping area having a first engagement section;
   a collet tubular member;
   a delivery tubular member, said delivery tubular member in coaxial association with said collet tubular member, said delivery tubular member having a second engagement section located on its distal section;
   an injection tubular member; said injection tubular member in coaxial association with said delivery tubular member;
   an introducer tubular member, said introducer in coaxial association with said delivery tubular member;
   a guiding member, said guiding member in coaxial association with said introducer tubular member.

2. The apparatus for treating a spinal disc as recited in claim 1, whereby a portion of said overlapping area has a threaded nut section designed to removable engage a screw section on said delivery tubular member.

3. The apparatus for treating a spinal disc as recited in claim 1, whereby the deliver tubular member enters the interior chamber through a opening hole in said inner mesh and has removable engaging section in the overlapping area.

4. The apparatus for treating a spinal disc as recited in claim 1, whereby the deliver tubular member enters the interior chamber through a channel or pouch between said and has removable engaging section in the overlapping area.

5. The apparatus for treating a spinal disc as recited in claim 1, whereby said portion of said inner mesh has an overlapping section with said outer mesh is designed to have a self-sealing capacity upon the removal of said delivery tubular member.

6. The apparatus for treating a spinal disc as recited in claim 5, whereby said self-sealing is achieved by two opposing materials are engaged by internal pressure, external pressure, or both internal and external pressure.

7. The apparatus for treating a spinal disc as recited in claim 1, whereby one or more injectable materials are delivered in said interior chamber of said mesh through said injection tubular member.

8. The apparatus for treating a spinal disc as recited in claim 7, wherein said one or more injectable materials are delivered in a controlled process to various locations around the circumference of the flexible and expandable mesh.

9. The apparatus for treating a spinal disc as recited in claim 7, whereby said one or more injectable materials are delivered by air pressure.

10. The apparatus for treating a spinal disc as recited in claim 7, whereby said one or more injectable materials are delivered by a mechanical means.

11. The apparatus for treating a spinal disc as recited in claim 7, whereby said one or more injectable materials are delivered by an electromechanical means.

12. The apparatus for treating a spinal disc as recited in claim 7, whereby said one or more injectable materials are delivered by a hydrodynamic means.

13. The apparatus for treating a spinal disc as recited in claim 7, whereby said one or more injectable materials are delivered by vibratory or oscillatory energy means.

14. A method of treating a diseased inter-vertebral disc, comprising the steps of:
creating an access opening in a disc between the adjacent vertebrae;
removing at least a portion of an nucleus within said disc which results in forming a cavity surrounding by a portion of the annulus of said disc;
advancing into the cavity a flexible and expandable substantially tubular braided mesh having an interior section in slidable and coaxial cooperation with an outer section, said expandable mesh attached to a delivery tubular member through an insertion opening, said delivery tubular member having an inner lumen;
advancing a guiding member through the inner lumen of said delivery tubular member;
advancing an introducer tubular member and an injection tubular member coaxially over said guiding member whereby said introducer tubular member and said injection tubular member expand said cavity and the flexible and expandable substantially tubular braided mesh;
retracting said introducer tubular member and said guiding member;
injecting one or more materials through said injection tubular member in said cavity;
retracting said injection tubular member; and
detaching said delivery tubular member whereby said access opening is self-sealed.

15. The method of treating a diseased inter-vertebral disc as recited in claim 14, wherein said one or more materials are formed of a material selected from the group consisting of hydrophilic polymers, hydrogels, homopolymer hydrogels, copolymer hydrogels, multi-polymer hydrogels, or interpenetrating hydrogels, acrylonitrile, acrylic acid, acrylimide, acrylimidine, including but not limited to PVA, PVP, PHEMA, PNVP, polyacrylainides, poly(ethylene oxide), polyvinyl alcohol, polyarylonitrile, and polyvinyl pyrrolidone, silicone, polyurethanes, polycarbonate-polyurethane (e.g., Corethane) other biocompatibile polymers, or combinations thereof.

16. The method of treating a diseased inter-vertebral disc as recited in claim 14, wherein said materials are formed of a material that is allowed to expand through the adsorption of liquids such as water selected from the group consisting of polyacrliamide, polyacrylonitrile, polyvinyl alcohol or other biocompatible hydrogels, solid fibrous collagen or other suitable hydrophilic biocompatible material or combinations thereof.

17. The method of treating a diseased inter-vertebral disc as recited in claim 14, wherein said materials are formed of a material selected from the group consisting of steroids, antibiotics, tissue necrosis factor alpha or its antagonists, analgesics, growth factors, genes or gene vectors in solution; biologic materials (hyaluronic acid, non-crosslinked collagen, fibrin, liquid fat or oils); synthetic polymers (polyethylene glycol, liquid silicones, synthetic oils), saline or combinations thereof.

18. The method of treating a diseased inter-vertebral disc as recited in claim 14, wherein said materials are formed of a material selected from the group consisting of bone graft materials such as any described "bone cements" or any polymeric bone graft compounds, bone graft materials, bone chips, nylon fibers, carbon fibers, glass fibers, collagen fibers, ceramic fibers, polyethylene fibers, polypropylene fibers, poly(ethylene terephthalate), polyglycolides, polylactides, and combinations thereof.

19. The method of treating a diseased inter-vertebral disc as recited in claim 14, wherein said materials are formed from calcium phosphate-based bone substitutes such as monolithic tetracalcium phosphate $(CA_4(PO_4)_2O)$.

20. The method of treating a diseased inter-vertebral disc as recited in claim 19, further comprising minor amounts of additional substances, such as $Na_3PO_4$; $Na_2HPO_4$; $NaH_2PO_4$; $Na_4HPO_4.7H_2O$; $Na_3PO_4.12H_2O$; $H_3PO_4$; $CaSO_4$; $(NH_4)_3PO_4$; $(NH_4)_2HPO_4$; $(NH_4)H_2PO_4$; $(NH_4)_3PO_4.3H_2O$; $NaHCO_3$; $CaCO3$; $Na_2CO_3$; $KH_2PO_4$; $K_2HPO_4$; $K_3PO_4$; $CaF_2:SSrF_2$; $Na_2SiF_6$; $Na_2PO_3F$, and combinations thereof.

21. The method of treating a diseased inter-vertebral disc according to claim 14 or 19, further comprising an amount of one or more active agents suitable to promote bone growth, such as a growth factor, BMP, a bone morphology protein, or a pharmaceutical carrier, and combination thereof.

22. An apparatus for treating a spinal disc comprising:
a flexible and expandable braided, woven, knitted or embroidered mesh, said mesh having an inner mesh section in slidable and coaxial cooperation with an outer mesh section, said mesh further having an interior chamber and an inner section; a portion of said inner mesh overlaps within said outer mesh resulting in a overlapping area, said overlapping area having a first engagement section;
a delivery tubular member, said delivery tubular member having a second engagement section located on its distal end;

an injection tubular member; said injection tubular member in coaxial association with said delivery tubular member;

an introducer tubular member, said introducer in coaxial association with said delivery tubular member; and a guiding member, said guiding member in coaxially association with said introducer tubular member.

23. The apparatus for treating a spinal disc as recited in claim 22, whereby a portion said overlapping area has a threaded nut section designed to engage said screw section on said delivery tubular member.

24. The apparatus for treating a spinal disc as recited in claim 22, whereby the deliver tubular member enters the interior chamber through a opening hole in said inner mesh and has removable engaging section in the overlapping area.

25. The apparatus for treating a spinal disc as recited in claim 22, whereby the deliver tubular member enters the interior chamber through a channel or pouch between said and has removable engaging section in the overlapping area.

26. The apparatus for treating a spinal disc as recited in claim 22, whereby said portion of said inner mesh overlaps within said outer mesh is designed to have a self-sealing capacity upon the removal of said delivery tubular member.

27. The apparatus for treating a spinal disc as recited in claim 22, whereby said self-sealing is achieved by two opposing materials are engaged by internal pressure, external pressure, or both internal and external pressure.

28. The apparatus for treating a spinal disc as recited in claim 22, whereby one or more injectable materials are delivered in said interior chamber of said mesh through said injection tubular member.

29. The apparatus for treating a spinal disc as recited in claim 28, wherein said one or more injectable materials are delivered in a controlled process to various locations around the circumference of the flexible and expandable mesh.

30. The apparatus for treating a spinal disc as recited in claim 28, whereby said one or more injectable materials are delivered by air pressure.

31. The apparatus for treating a spinal disc as recited in claim 28, whereby said one or more injectable materials are delivered by a mechanical means.

32. The apparatus for treating a spinal disc as recited in claim 28, whereby said one or more injectable materials are delivered by a electromechanical means.

33. The apparatus for treating a spinal disc as recited in claim 28, whereby said one or more injectable materials are delivered by a hydrodynamic means.

34. The apparatus for treating a spinal disc as recited in claim 28, whereby said one or more injectable materials are delivered by vibratory or oscillatory energy means.

35. The apparatus for treating a spinal disc as recited in claim 22, whereby said delivery tubular member has a removable attachment means that is design to removably engage said guiding member.

* * * * *